(12) United States Patent
Moshkovitz et al.

(10) Patent No.: US 10,943,163 B2
(45) Date of Patent: Mar. 9, 2021

(54) METHODS AND SYSTEMS FOR SECURING, DELIVERING, AND MONITORING USE OF AN ACTIVE AGENT

(71) Applicant: Intel Corporation, Santa Clara, CA (US)

(72) Inventors: Ariel Moshkovitz, Haifa (IL); Oren Arad, Palo Alto, CA (US); Tomer Rider, Naahryia (IL); Tamara Gaidar, Haifa (IL); Oleg Pogorelik, Lapid (IL)

(73) Assignee: Intel Corporation, Santa Clara, CA (US)

( * ) Notice: Subject to any disclaimer, the term of this patent is extended or adjusted under 35 U.S.C. 154(b) by 4 days.

(21) Appl. No.: 16/235,946

(22) Filed: Dec. 28, 2018

(65) Prior Publication Data
US 2019/0205716 A1 Jul. 4, 2019

Related U.S. Application Data

(60) Provisional application No. 62/612,256, filed on Dec. 29, 2017.

(51) Int. Cl.
*G06K 19/073* (2006.01)
*H04L 29/06* (2006.01)
(Continued)

(52) U.S. Cl.
CPC ........ *G06K 19/07354* (2013.01); *A61J 1/035* (2013.01); *A61J 3/007* (2013.01);
(Continued)

(58) Field of Classification Search
CPC . G06K 19/07354; A61J 7/0418; A61J 7/0436; A61J 1/035; A61J 3/007;
(Continued)

(56) References Cited

U.S. PATENT DOCUMENTS

2007/0282252 A1* 12/2007 Stukanov ............. A61K 9/0009
604/93.01
2009/0167531 A1* 7/2009 Ferguson ............ G06F 19/3462
340/572.1

(Continued)

OTHER PUBLICATIONS

Editor; "E Ink, HTC and Palladio Collaborate to Develop Smart Label for IoT-Based Healthcare Services;" The OSA Direct Newsletter; (Oct. 4, 2016); 3 pages.
(Continued)

*Primary Examiner* — Mohamed Barakat
(74) *Attorney, Agent, or Firm* — Hanley, Flight and Zimmerman, LLC

(57) ABSTRACT

Technologies are described for delivering an active agent using an ingestible pill device, securing medication package content, and monitoring the medication package content. Examples of the technology include using an ingestible pill device to deliver an active agent, where release of the active agent can be based on patient authentication, analyzing sensor data to determine a condition for releasing the active agent, analyzing image data to identify a release point, etc. Examples of the technology also include using a monitoring device to secure a medication package using a cover and locking device, monitoring the medication package to detect access to the medication package, and tracking access to the medication package to determine medication adherence.

22 Claims, 20 Drawing Sheets

(51) Int. Cl.
*A61J 1/03* (2006.01)
*A61J 3/00* (2006.01)
*G01N 21/90* (2006.01)
*A61J 7/04* (2006.01)
*A61M 31/00* (2006.01)

(52) U.S. Cl.
CPC ............ *A61J 7/0418* (2015.05); *A61J 7/0436* (2015.05); *A61M 31/002* (2013.01); *G01N 21/90* (2013.01); *H04L 63/0861* (2013.01); *A61J 2200/30* (2013.01); *A61J 2200/70* (2013.01); *A61J 2205/60* (2013.01)

(58) Field of Classification Search
CPC ................ A61J 2200/30; A61J 2200/70; A61J 2205/60; A61M 31/002; G01N 21/90; H04L 63/0861
See application file for complete search history.

(56) References Cited

U.S. PATENT DOCUMENTS

| | | | | |
|---|---|---|---|---|
| 2010/0121315 | A1* | 5/2010 | Trovato | H04L 9/3278 604/890.1 |
| 2010/0222670 | A1* | 9/2010 | Demierre | A61B 5/065 600/424 |
| 2014/0288942 | A1* | 9/2014 | Blochet | A61J 7/04 705/2 |
| 2015/0259110 | A1* | 9/2015 | Blackburn | A61J 7/0076 222/1 |
| 2015/0343144 | A1* | 12/2015 | Altschul | A61B 5/14542 604/503 |

OTHER PUBLICATIONS

Information Mediary Corp.; "Med-ic® Mobile Adherence Packaging Innovations;" [Brochure]; (2017); 2 pages.

Information Mediary Corporation; "Med-ic® Smart Label;" www.informationmediary.com/med-ic; (Jan. 1, 2017); 2 pages; [retrieved Apr. 29, 2019]; Retrieved from <URL: https://web.archive.org/web/20170101095105/http://www.informationmediary.com/med-ic>.

Mack; "Report: Pharma Loses $637B Annually Due to Medication Nonadherence;" MobiHealthNews; (Nov. 16, 2016); 6 pages; [retrieved on Jun. 28, 2019]; Retrieved from <URL: https://www.mobihealthnews.com/content/report-pharma-loses-637b-annually-due-medication-nonadherence>.

Plus Plastic Electronics; "Stora Enso and NXP Collaborate on Smart Packaging;" https://www.plusplasticelectronics.com/retail/stora-enso-and-nxp-collaborate-on-smart-packaging; (Oct. 7, 2015); 3 pages; [retrieved Apr. 29, 2019]; Retrieved from <URL: https://web.archive.org/web/20151007231716/https://www.plusplasticelectronics.com/retail/stora-enso-and-nxp-collaborate-on-smart-packaging>.

Poor; "Smart Pill Delivers Drugs Where Needed;" Health Tech Insider; (Jul. 17, 2015); 2 pages.

Proteus Digital Health Inc.; "Proteus Digital Health;" https://www.proteus.com/ ; (Jan. 20, 2017); 6 pages; [retrieved Apr. 29, 2019] ; Retrieved from <URL: https://web.archive.org/web/20170120174001/http://www.proteus.com/>.

Proteus Digital Health; "Otsuka and Proteus® Announce the First U.S. FDA Approval of a Digital Medicine System: Abilify MyCite® (Aripipraxole Tablets with Sensor);" (Nov. 14, 2017); 6 pages.

Westrock Company; "Cerepak® Smart Adherence Packaging;" www.westrock.com/en/products/folding-cartons/cerepak; (Nov. 28, 2016); 3 pages; [retrieved Apr. 29, 2019]; Retrieved from <URL: https://web.archive.org/web/20161128003801/https://www.westrock.com/en/products/folding-cartons/cerepak>.

* cited by examiner

METHODS AND SYSTEMS FOR SECURING, DELIVERING, AND MONITORING USE OF AN ACTIVE AGENT

RELATED APPLICATION

This application is related to U.S. Provisional Application No. 62/612,256 filed on Dec. 29, 2017, which is incorporated herein by reference.

BACKGROUND

Proper patient compliance in taking prescribed medication is of paramount importance in achieving intended pharmacotherapy benefits. Proper compliance ultimately encompasses all activities required for a patient to receive intended medication dosing, including factors such as getting prescriptions filled, remembering to take medication on time, and taking medication according to any accompanying directions (e.g. with food, without food, etc.). Poor patient compliance can undermine the intended pharmacotherapy effects and negate treatment benefits.

Chronic illnesses or conditions commonly require long-term pharmacotherapy. While sustained treatment can provide ongoing relief for most patients, maintaining a medicinal regimen over months or years can prove challenging. Likewise, challenges can be encountered when using pharmacotherapy to treat an acute illness or condition which may only require limited-time therapy. Since a patient has not previously taken the required medication, remember to follow a newly introduced regimen may be problematic. Whether in the short or long term, medication monitoring can improve overall patient compliance and boost the effectiveness of prescribed pharmacotherapy.

One issue related to compliance is medication safety. Poor adherence to taking a medication correctly can result in misuse and/or accidental dosing. For example, failing to complete a drug regimen can leave unused medication available for misuse or accidental ingestion. Various techniques have been used to help mitigate misuse and accidental dosing of medications. For example, locking caps can be used to help prevent a child from accessing a prescription bottle containing a medication. Other containers may have features that can be used help track compliance and whether a drug regimen has been completed. However, these techniques have not been entirely successful in preventing an individual from wrongly or accidently taking a medication. Furthermore, proper compliance has not always been assured.

For many patients, accurately delivering a medication to a treatment area may improve the treatment of a condition. For example, conditions within the gastrointestinal (GI) tract, such as inflammatory bowel disease (IBD), intestinal cancers, and irritable bowel syndrome (IBS), may be better treated by delivering an active agent to an effected area in the GI tract. Moreover, some medicines or active agents are more bioavailable when released in the stomach or upper GI tract instead of the intestines or lower GI tract. The ability to identify a treatment area, or target release area, and deliver a medication accordingly can provide advantages such as better effectiveness of an active agent and potentially improving overall patience health.

BRIEF DESCRIPTION OF THE DRAWINGS

Features and advantages of example technology embodiments will be apparent from the detailed description which follows, taken in conjunction with the accompanying drawings, which together illustrate examples of the technology; and, wherein.

Figure 1:
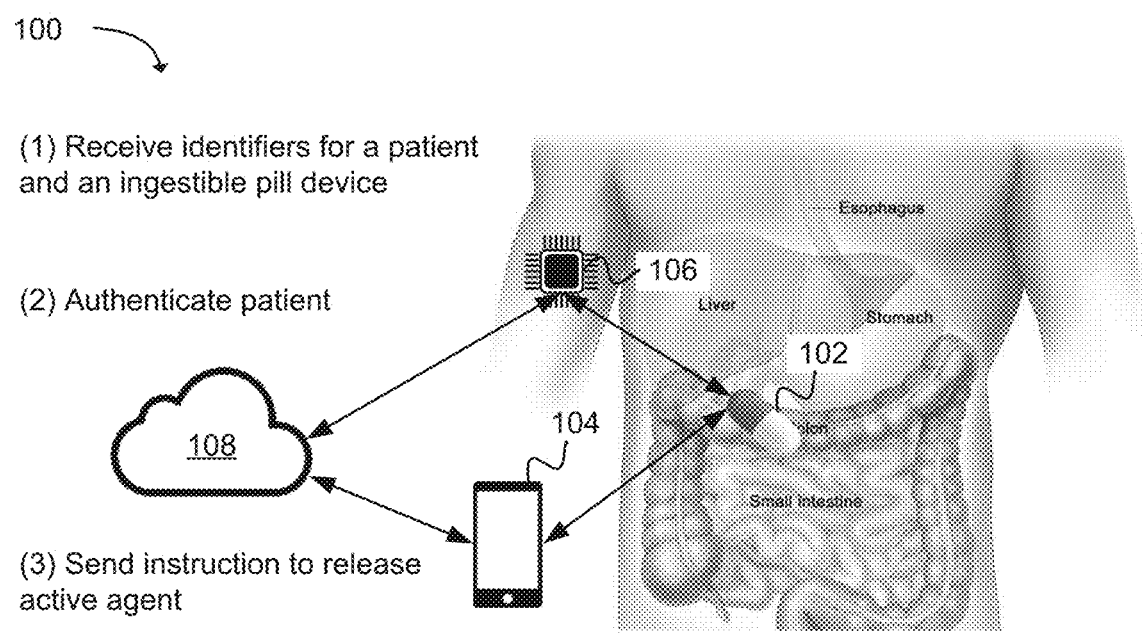
FIG. 1 is a diagram illustrating a system and method for identifying and authenticating a patient, and releasing an active agent contained in a pill device to a release point located in the patient's GI tract.

These drawings are provided to illustrate various aspects of the technology and are not intended to be limiting of the scope in terms of dimensions, materials, configurations, arrangements, or proportions unless otherwise limited by the claims.

DESCRIPTION OF THE TECHNOLOGY

Before examples of the technology are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of layouts, distances, network examples, etc., to provide a thorough understanding of various examples. One skilled in the relevant art will recognize, however, that such detailed embodiments do not limit the overall inventive concepts articulated herein, but are merely representative thereof.

As used in this written description, the singular forms "a," "an" and "the" include express support for plural referents unless the context clearly dictates otherwise. Thus, for example, reference to "a network" includes a plurality of such networks.

Reference throughout this specification to "an example", "an embodiment", or "an aspect" means that a particular feature, structure, or characteristic described in connection with the example is included in at least one example embodiment. Thus, occurrences of the phrases "an example", "in one example", "an embodiment", "in one embodiment", or "in one aspect" in various places throughout this specification are not necessarily all referring to the same embodiment, example, or aspect.

As used herein, a plurality of items, structural elements, compositional elements, and/or materials can be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various examples can be referred to herein along with alternatives for the various components thereof. It is understood that such embodiments, examples, and alternatives are not to be construed as defacto equivalents of one another, but are to be considered as separate and autonomous representations under the present disclosure.

Furthermore, the described features, structures, or characteristics can be combined in any suitable manner in one or more embodiments. In the following description, numerous specific details are provided, such as examples of layouts, distances, network examples, etc., to provide a thorough understanding of example embodiments. One skilled in the relevant art will recognize, however, that the technology can be practiced without one or more of the specific details, or with other methods, components, layouts, etc. In other instances, well-known structures, materials, or operations may not be shown or described in detail to avoid obscuring aspects of the disclosure.

In this application, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in this written description, like "comprising" or "including," it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "improved," "worse," "higher," "lower," "enhanced," and the like refer to a property of a device, component, or activity that is measurably different from other devices, components, or activities in a surrounding or adjacent area, in a single device or in multiple comparable devices, in a group or class, in multiple groups or classes, or as compared to the known state of the art.

The term "coupled," as used herein, is defined as directly or indirectly connected in an electrical or nonelectrical manner. "Directly coupled" structures or elements are in physical contact with one another and are attached. Objects described herein as being "adjacent to" each other may be in physical contact with each other, in close proximity to each other, or in the same general region or area as each other, as appropriate for the context in which the phrase is used.

Numerical amounts and data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5"

should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 1.5, 2, 2.3, 3, 3.8, 4, 4.6, 5, and 5.1 individually.

This same principle applies to ranges reciting only one numerical value as a minimum or a maximum. Furthermore, such an interpretation should apply regardless of the breadth of the range or the characteristics being described.

As used herein, the terms "therapeutic agent," "active agent," and the like can be used interchangeably and refer to any agent that can have a beneficial or positive effect on a subject when administered to the subject in an appropriate or effective amount.

As used herein, an "effective amount" of an agent is an amount sufficient to accomplish a specified task or function desired of the agent. A "therapeutically effective amount" of a composition, drug, or agent refers to a non-toxic, but sufficient amount of the composition, drug, or agent, to achieve therapeutic results in treating or preventing a condition for which the composition, drug, or agent is known to be effective. It is understood that various biological factors may affect the ability of a substance to perform its intended task. Therefore, an "effective amount" or a "therapeutically effective amount" may be dependent in some instances on such biological factors. Further, while the achievement of therapeutic effects may be measured by a physician, veterinarian, or other qualified medical personnel using evaluations known in the art, it is recognized that individual variation and response to treatments may make the achievement of therapeutic effects a somewhat subjective decision. The determination of an effective amount or therapeutically effective amount is well within the ordinary skill in the art of pharmaceutical sciences and medicine. See, for example, Meiner and Tonascia, "Clinical Trials: Design, Conduct, and Analysis," Monographs in Epidemiology and Biostatistics, Vol. 8 (1986).

As used herein, a "dosing regimen" or "regimen" such as "treatment dosing regimen," or a "prophylactic dosing regimen" refers to how, when, how much, and for how long a dose of an active agent or composition can or should be administered to a subject in order to achieve an intended treatment or effect.

As used herein, the terms "treat," "treatment," or "treating" refers to administration of a therapeutic agent to subjects who are either asymptomatic or symptomatic. In other words, "treat," "treatment," or "treating" can be to reduce, ameliorate or eliminate symptoms associated with a condition present in a subject, or can be prophylactic, (i.e. to prevent or reduce the occurrence of the symptoms in a subject). Such prophylactic treatment can also be referred to as prevention of the condition.

As used herein, the terms "formulation" and "composition" are used interchangeably and refer to a mixture of two or more compounds, elements, or molecules. In some aspects the terms "formulation" and "composition" may be used to refer to a mixture of one or more active agents with a carrier or other excipients. Compositions can take nearly any physical state, including solid, liquid (i.e. solution), or gas. Furthermore, the term "dosage form" can include one or more formulation(s) or composition(s) provided in a format for administration to a subject. For example, an injectable dosage form would be a formulation or composition prepared in a manner that is suitable for administration via injection.

As used herein, a "subject" refers to an animal. In one aspect the animal may be a mammal. In another aspect, the mammal may be a human.

EXAMPLE EMBODIMENTS

An initial overview of technology embodiments are provided below and specific technology embodiments are then described in further detail. This initial summary is intended to aid readers in understanding the technologies more quickly, but is not intended to identify key or essential technological features, nor is it intended to limit the scope of the claimed subject matter.

Example Embodiments for Activating and Delivering an Active Agent Using an Ingestible Pill Device Technology is described for delivering an active agent using an ingestible pill device. The ingestible pill device may be an ingestible capsule configured with sensors used to, for example, measure pH (potential of hydrogen), temperature, pressure, as well as other conditions of a GI (Gastrointestinal) tract. The ingestible pill device may contain an active agent, such as a pharmaceutical drug, that can be released after one or more conditions have been met. As described herein, identification and authentication techniques can be used to set rules and control provisioning of an active agent contained in an ingestible pill device (hereinafter "pill device").

To further describe the technology, examples are provided with reference to the figures. FIG. 1 is a diagram illustrating an example of a general system 100 for identifying and authenticating a patient, and releasing an active agent contained in a pill device 102 to a release point located in the patient's GI tract. As illustrated, the system 100 can include a pill device 102 configured to wirelessly communicate with an authenticator device, such as a mobile device 104 and/or an implantable device 106, which may be in communication with one or more services hosted in a computing services environment (e.g., "cloud" services).

The pill device 102 may contain an active agent prescribed to a patient by a physician. As part of prescribing the active agent to the patient, a drug provisioning service 108 hosted in the computing service environment can be used to ensure that the active agent is ingested by a patient who is authorized to take the active agent, and not by an unauthorized person, such as a child, caregiver, or other third party. For example, an active agent provider, such as a physician, pharmacist, caregiver, and the like, may use the drug provisioning service 108 to provision pill devices 102 to patients and specify dosages, instructions, expiration dates, recall requests, etc. for the pill devices 102. The pill device 102 can include an embedded pill identifier that can be linked to patient information (e.g., a patient identifier, patient record, patient prescription, etc.) using the drug provisioning service 108. For example, as part of prescribing an active agent to a patient, the active agent provider can use the drug provisioning service 108 to link a pill identifier for a pill device 102 to a patient identifier for a patient prescribed the active agent. As such, the pill identifier can be linked to a prescription for the active agent. The active agent provider can also use the drug provisioning service 108 to specify rules for taking a pill device 102, such as, for example: prescription instructions specifying a pH level at which the active agent can be released, a temperature at which the active agent can be released, drug-to-drug and/or drug-to-food interaction rules, as well as other rules used to determine when and/or whether to release an active agent contained in the pill device 102.

The pill device 102 can be activated using an identification and authentication process to identify and authenticate a patient prescribed the pill device 102. Activating the pill device 102 may place the pill device 102 in a state that allows the pill device 102 to release the active agent contained in the pill device 102. The identification and authentication process may be performed using an authenticator device, such as a mobile device 104, a stationary device (not shown), and/or an implantable device 106, configured to connect to the drug provisioning service 108. For example, an authenticator device (e.g. electronic device, stationary device, mobile device 104, or implantable device 106) may pair with a pill device 102 (e.g., via BLE, WiFi, NFC, etc.) and obtain an embedded pill identifier from the pill device 102. For example, the patient device 104/106 may obtain patient credentials (e.g., a username/password or security certificate) from a patient, or from a storage location on the device 104/106, and send the pill identifier and the patient credentials to the drug provisioning service 108. The drug provisioning service 108 may use the patient credentials to identify the patient and authenticate the patient credentials, and use the pill identifier to determine whether the patient has been prescribed the active agent contained in the pill device 102.

In the case that identification and authentication is successful, the drug provisioning service 108 sends a release instruction to the device 104/106 and the device 104/106 forwards the release instruction to the pill device 102. The pill device 102 receives the release instruction from the device 104/106 and releases the active agent. In one example, release instructions can include one or more condition precedents that need to be satisfied prior to releasing an active agent contained in a pill device 102. For example, a release instruction may include a condition to release the active agent after detecting a pH that meets a pH threshold for releasing the active agent, or an instruction to release a defined amount of the active agent at staged intervals according to a dosing schedule. Alternatively, a release instruction may include a condition that verifies the pill is inside the GI tract of a patient, of example, with pH, optical, or other sensory information provided by the pill. Yet further, a release instruction may include a condition that verifies the time and amount of a prior dosage, or of the timing and amount of doses of other medication to the patient. In the case that release criteria instructions are not met (e.g. identification and/or authentication failure), the drug provisioning service 108 may send a message to the device 104/106 indicating that release criteria failed, and the active agent in the pill device 102 may not be released. In this case, the pill would simply pass through the patient with no pharmacological effect. Furthermore, in the event of a failure, the prescribing pharmacist, physician, or other entity, person, or service may be notified. Notification can be used to monitor compliance, or misuse.

In one example, identification and authentication may be performed prior to ingesting a pill device 102. For example, a patient may use a mobile device 104 to perform identification and authentication, which activates a pill device 102, and thereafter, ingest the pill device 102 allowing an active agent contained in the pill device 102 to be released in the patient's stomach or other location in the GI tract. In another example, identification and authentication may be performed after ingesting a pill device 102. For example, after being ingested, the pill device 102 may detect a biologic identifier via an optical image, a pH, a temperature, a cellular structure or property, etc., confirming that the pill device 102 has been ingested and/or is located within a proximity of a treatment area, at which point, causes the pill device 102 to pair with an implantable device 106, allowing identification and authentication to be performed, and after successful identification and authorization, the pill device 102 may release an active agent.

Figure 2:
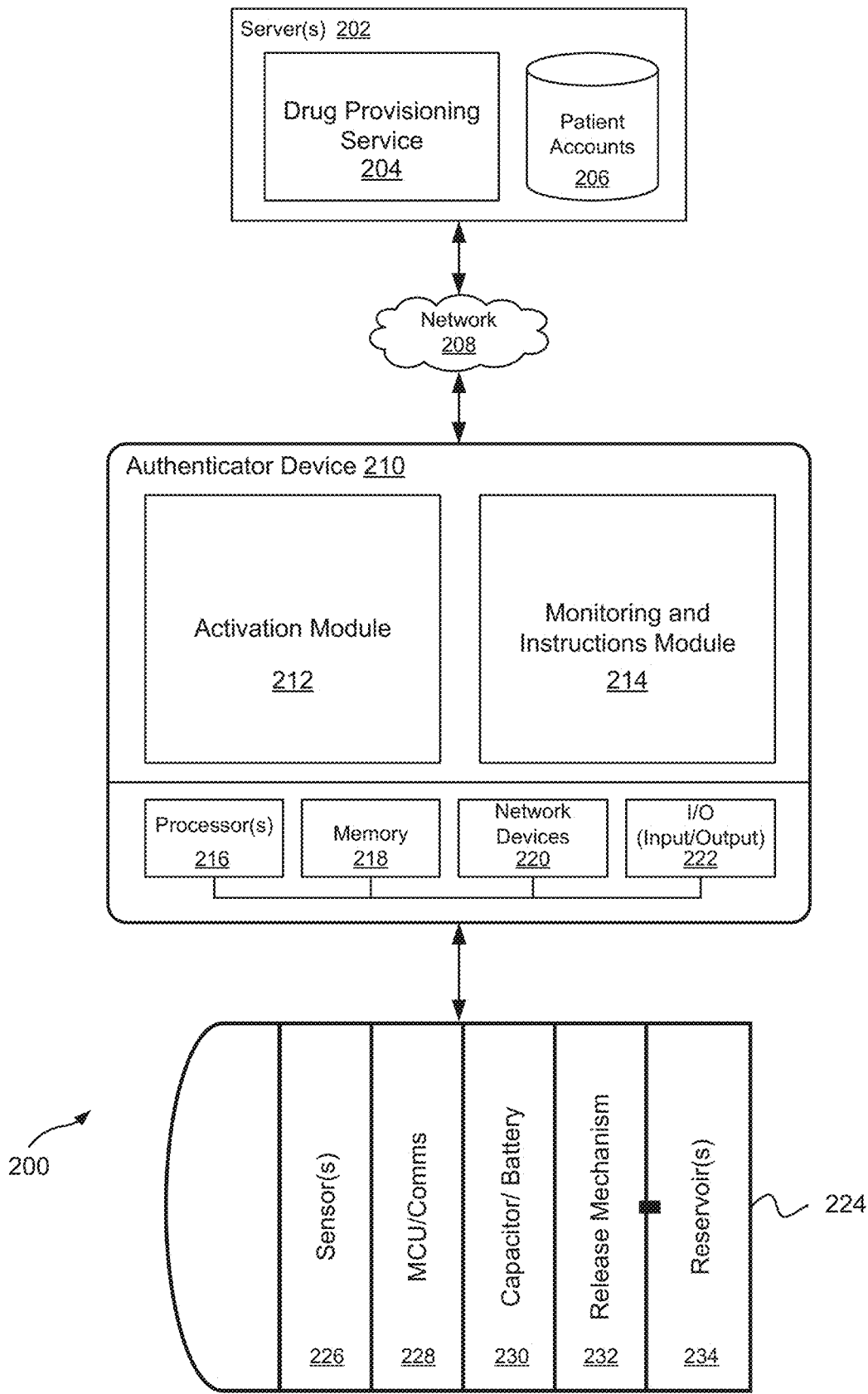
FIG. 2 is a block diagram that illustrates components of an example system for delivering an active agent using a pill device.

FIG. 2 illustrates components of an example system 200 for delivering an active agent using a pill device 224. The pill device 224 may be configured to release an active agent after the successful completion of an identification and authentication process. As illustrated, the pill device 224 can include sensors 226 that can be used to detect GI tract environment conditions. For example, the sensors 226 may include a pH sensor, a temperature sensor, a GPS (Global Positioning System) sensor, an optical sensor, a chemical sensor, a cellular material sensor, as well as other sensors. The pill device 224 may include a MCU (Microcontroller Unit) and a communication module 228 used to connect to, and communicate with, an authenticator device 210 (e.g., a stationary electronic device, a mobile device, or an implantable device). For example, the pill device 224 may include a transceiver used to communicate with the authenticator device 210 using a short-range communication protocol, such as, but not limited to: BLUETOOTH, BLE (Bluetooth Low Energy), ZigBee, Z-Wave, NFC (Near Field Communication), RFID (Radio Frequency Identification), and other short-range communication protocols. Communications between the pill device 224 and the authenticator device 210 may be associated with the identification and authentication process, and to execute release instructions that activate a release mechanism 232 and release an active agent contained in a reservoir 234 of the pill device 224. Also, the pill device 224 can include an energy source, such as a capacitor or battery 230, used to power the components of the pill device 224.

The authenticator device 210 can include an activation module 212 configured to control activation of the pill device 224 via the identification and authentication process. In one example, the authenticator device 210 may be configured to detect and pair with the pill device 224 (e.g., via BLE scanning, etc.), and send a notification to the activation module 212 that the pill device 224 has been detected. In one example, after pairing with the pill device 224, the activation module 212 obtains an embedded device identifier from the pill device 224. The activation module 212 obtains patient credentials, which may be stored in memory 218 on the authenticator device 210, or obtained from a patient via a user interface (not shown), and the activation module 212 sends an authentication and activation request (e.g., an API request) to the drug provisioning service 204 that includes the patient credentials and the device identifier. In the case that authentication is successful, the activation module 212 receives an activation message from the drug provisioning service 204 indicating permission to activate the pill device 224. The activation module 212 then sends instructions to the pill device 224 using a short-range communication protocol to release the active agent contained in the reservoir of the pill device 224. In response to receiving the instructions from the activation module 212, the pill device 224 releases the active agent by activating a release mechanism 232 which opens a reservoir 234 containing the active agent.

The drug provisioning service 204 can be configured to authenticate patient credentials and provide permission to activate the pill device 224. In one example, the drug provisioning service 204 receives authentication and activation requests from the activation module 212 and identifies a patient account 206 associated with patient credentials and authenticates the patient credentials using authenticating information included in the patient account 206. After authenticating the patient credentials, the drug provisioning service 204 then references the patient account 206 to determine whether the patient associated with the patient account 206 has been prescribed the pill device 224 by cross referencing the device identifier with a patient prescription. In determining that the patient has been prescribed the pill device 224, the drug provisioning service 204 sends an activation message to the activation module 212 indicating permission to activate the pill device 224.

In another example, the activation module 212 may be configured to activate the pill device 224 after successful authentication of patient credentials (e.g., a password, PIN, biometric identifier, etc.). As described earlier, a copy of the patient credentials may be stored on the authenticator device 210 (e.g., encrypted in memory 218), and the activation module 212 may authenticate the patient credentials provided by the patient using the copy of the patient credentials stored on the authenticator device 210. After successful authentication of the patient credentials, the activation module 212 sends instructions to the pill device 224 that activates the pill device 224. As an illustration, after ingesting the pill device 224, the patient may log into the patient's mobile device using a PIN, and after successful authentication of the patient's PIN, the activation module 212 sends instructions to the pill device 224 to release the active agent.

In yet another example, a secondary authentication may be used to activate the pill device 224. For example, a first authentication can be performed to verify that a child or dependent has been prescribed an active agent contained in a pill device 224 and a second authentication can be performed using parent or caregiver credentials. As an illustration, the activation module 212 may be configured to authenticate an identifier transmitted by the pill device 224 to the authenticator device 210 by sending the identifier to the drug provisioning service 204, which verifies that the pill device 224 has been prescribed to a child or dependent. In the case that the first authentication is successful, then the activation module 212 may be configured to prompt a parent or caregiver for credentials via a user interface. After successful authentication of the parent or caregiver credentials, the activation module 212 sends instructions activating the pill device 224.

In one example, the drug provisioning service 204 may provide a dosing schedule and/or dosing instructions to the authenticator device 210. The dosing schedule and/or dosing instructions can be obtained from a patient account 206 and the dosing schedule and/or dosing instructions can be provided to a monitoring and instructions module 214 hosted on the authenticator device 210. The monitoring and instructions module 214 can be configured to monitor sensor measurements for GI tract conditions provided by the pill device 224, and send instructions to release the active agent contained in the pill device 224 based on dosing schedule and/or dosing instructions. As an example, the monitoring and instructions module 214 may be used to monitor pH or other sensor data, such as optical data, temperature data, etc., received from the pill device 224 and detect that the sensor data meets a threshold specified in dosing instructions, and send an instruction to the pill device 224 to release an active agent contained in the pill device 224. As another example, the pill device 224 can include multiple reservoirs 234 containing one or more active agents and the active agents can be released according to a dosing schedule provided by the drug provisioning service 204.

The pill device 224, in one example, can provide confirmation that an active agent was released. For example, after releasing an active agent, the pill device 224 may send a notification to the authenticator device 210 indicating that the active agent was released. In response to receiving the notification, the monitoring and instructions module 214 may be configured to generate and/or update a record in a patient account 206 to indicate that the active agent was released. For example, a notification received from the pill device 224 can include information that includes a GI tract location where the active agent was released, a timestamp for when the active agent was released, an image of the release site, environment data for the release site (e.g., temperature data, pH data, chemical data, etc.), and the information can be written to a record included in a patient account 206. In one example, the pill device 224 can include a chemical sensor to detect that an active agent was released into a patient's GI tract, and in response to detecting the active agent in the GI tract, the pill device 224 can send a notification to the authenticator device 210 indicating that the active agent was detected in the patient's GI tract.

Patient accounts 203 may be stored in one or more data stores. The term "data store" may refer to any device or combination of devices capable of storing, accessing, organizing and/or retrieving data, which may include any combination and number of data servers, relational databases, object oriented databases, cluster storage systems, data storage devices, data warehouses, flat files and data storage configuration in any centralized, distributed, or clustered environment. The storage system components of the data store may include storage systems such as a SAN (Storage Area Network), cloud storage network, volatile or non-volatile RAM, optical media, or hard-drive type media. The data store may be representative of a plurality of data stores as can be appreciated.

API calls, procedure calls or other network commands that may be made in relation to the modules and services included in the system 200 may be implemented according to different technologies, including, but not limited to, Representational state transfer (REST) technology or Simple Object Access Protocol (SOAP) technology. REST is an architectural style for distributed hypermedia systems. A RESTful API (which may also be referred to as a RESTful web service) is a web service API implemented using HTTP and REST technology. SOAP is a protocol for exchanging information in the context of Web-based services.

A network 208 used by an authenticator device 210 to communicate with the server(s) 202 may include any useful computing network, including an intranet, the Internet, a local area network, a wide area network, a wireless data network, or any other such network or combination thereof. Components utilized for such a system may depend at least in part upon the type of network and/or environment selected. Communication over the network may be enabled by wired or wireless connections and combinations thereof.

FIG. 2 illustrates that certain processing modules may be discussed in connection with this technology and these processing modules may be implemented as computing services. In one example configuration, a module may be considered a service with one or more processes executing on a server or other computer hardware. Such services may be centrally hosted functionality or a service application that may receive requests and provide output to other services or consumer devices. For example, modules providing services may be considered on-demand computing that are hosted in a server, virtualized service environment, grid or cluster computing system. An API may be provided for each module to enable a second module to send requests to and receive output from the first module. While FIG. 2 illustrates an example of a system that may implement the techniques above, many other similar or different environments are possible. The example environments discussed and illustrated above are merely representative and not limiting.

Figure 3:
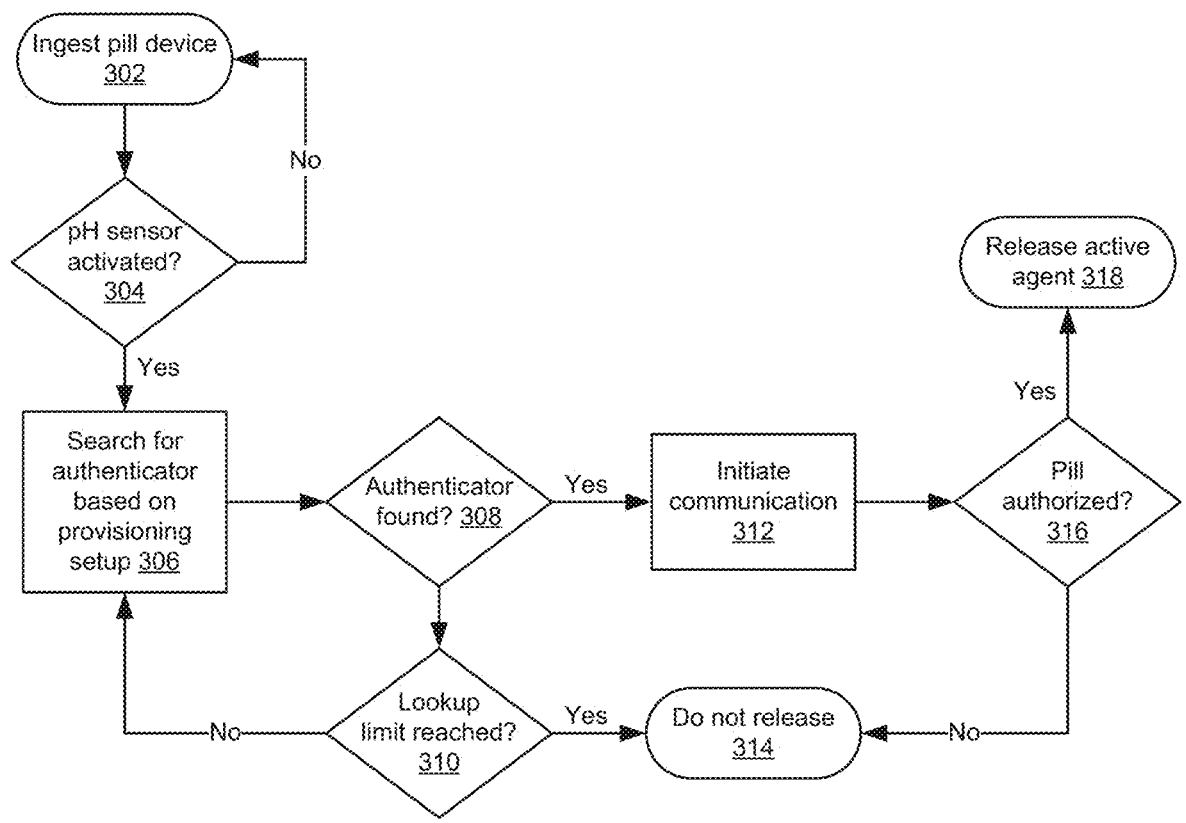
FIG. 3 is a flow diagram illustrating an example method for delivering an active agent using a pill device and an implantable device.

FIG. 3 is a flow diagram illustrating an example method for delivering an active agent using a pill device and an implantable device. A pill device provisioned to a patient may contain an active agent (e.g., pharmaceutical drug) prescribed to the patient. As part of provisioning the pill device, a healthcare provider may provide an authenticator used to authenticate the pill device. The authenticator may include a patient identifier (e.g., a unique identifier) that can be used by an implantable device to activate the pill device after ingestion of the pill device by the patient. Illustratively, an implantable device issued to a patient can be configured to store the patient identifier in memory of the implantable device, and a healthcare provider (e.g., a pharmacist) can store the patient identifier on a pill device (e.g., on a non-volatile memory module) using a data writer (e.g., a NFC or RFID writer). In one example, the patient identifier may be encrypted.

A pill device provisioned to a patient may be in an inactive state until communication with a patient device is established. The pill device can include a pH, or other sensor configured to detect a pH value that activates the pH sensor 304, or other optical or temperature value, etc., and causes the pill device to send a signal (e.g., a NFC or RFID signal) to the implantable device. After ingesting the pill device 302, sensor may detect a threshold value, or combination of values, such as pH, optical, temperature, and/or cellular values, and the pill device may send a signal. The implantable device may detect the signal sent by the pill device and search for an authenticator (the patient identifier) based on a provisioning setup 306 which stores the patient identifier in the memory of the implantable device. For example, the implantable device compares the patient identifier received from the pill device with the patient identifier stored on the implantable device. In one example, the implantable device may use an encryption key used to encrypt a patient identifier to decrypt the patient identifier, and the implantable device may authenticate the decrypted patient identifier using a patient identifier retrieved from the memory of the implantable device.

In the case that the authenticator (patient identifier) is found 308, then communication can be initiated 312 between the patient device and the pill device. After initiating communication 312, the pill device may release the active agent 318 contained in the pill device. In one example, after initiating communication 312, a healthcare provider, via a drug provisioning service, may initiate additional security procedures (e.g., authentication questions, PIN number, password, pattern, etc.) before authorizing the pill device 316 to release the active agent 318. Also, a healthcare provider, via a drug provisioning service, may provide prescription instructions to the implantable device and/or the pill device. For example, an instruction sent by the implantable device to a pill device may correspond to prescription instructions received from the drug provisioning service (e.g., release the active agent at a specified time or condition). As another example, the implantable device may send prescription instructions to a pill device, and the pill device may be configured to release an active agent according to the prescription instructions. In some examples, after releasing the active agent, the pill device may send a communication that the active agent was released, and a record stored on the implantable device or on another device or database, can be updated to indicate that the active agent was released. In the case that the authenticator cannot be found 308 (e.g., another device that is not the patient device tries to pair with the pill device), and a lookup limit has been reached 310, the pill device will not release 314 the active agent contained in the pill device.

Figure 4:
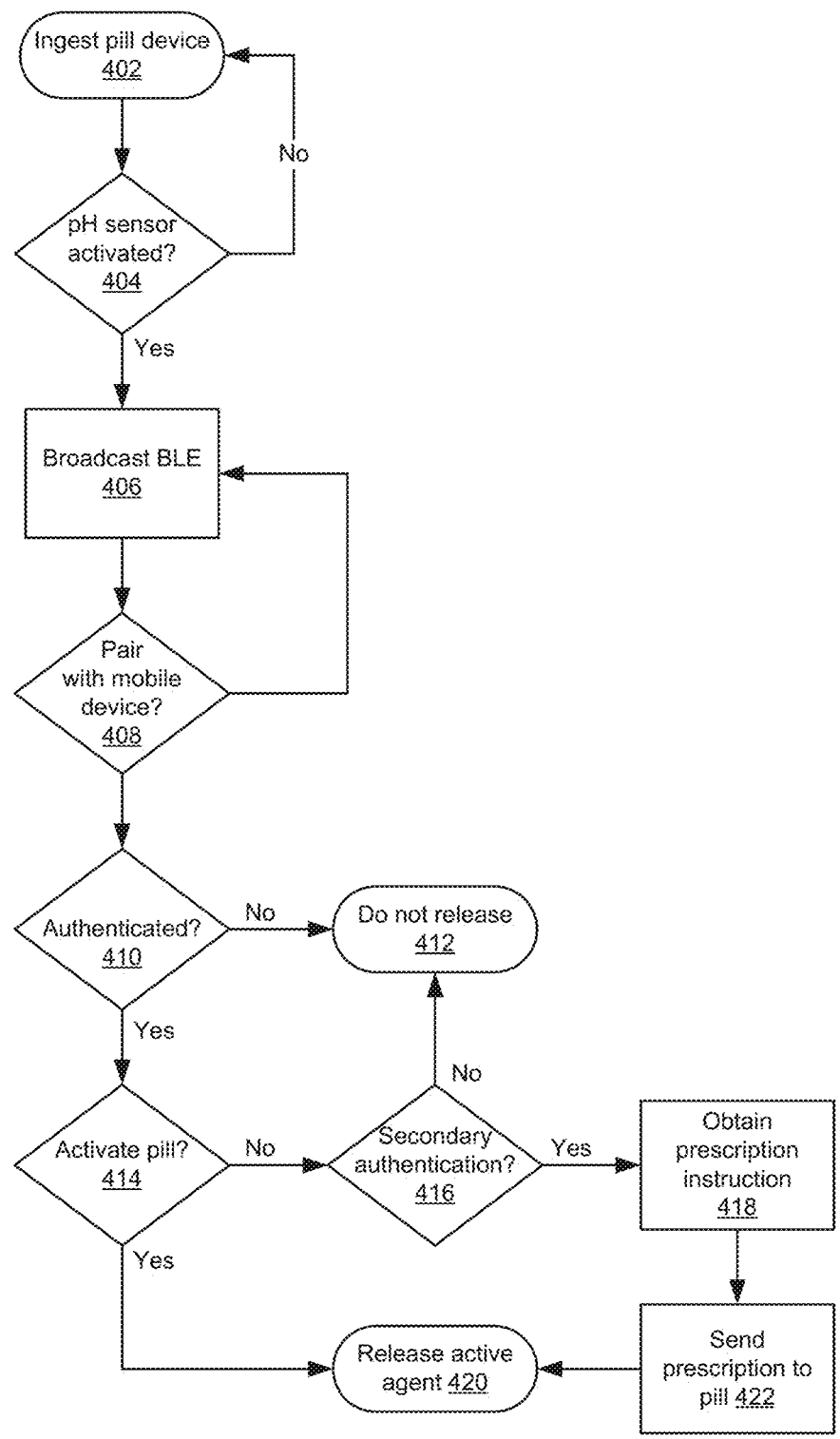
FIG. 4 is a flow diagram that illustrates an example method for delivering an active agent using a pill device and a mobile device.

FIG. 4 is a flow diagram illustrating an example method for delivering an active agent using a pill device and a mobile device. As part of provisioning a pill device, a healthcare provider may send a pill authenticator (e.g., pill identifier, device identifier, patient identifier, etc.) for the pill device to a patient's mobile device, as well as store the pill authenticator (e.g., using an NFC or RFID writer) on the pill device (e.g., on a non-volatile memory module). The pill authenticator can be used to authenticate and activate the pill device. The mobile device may use the pill authenticator to establish a network connection with the pill device. More specifically, the pill authenticator can be used as a pairing code or passkey to establish a BLUETOOTH connection between the mobile device and the pill device.

As illustrated, after ingesting the pill device 402, the pill device may be in an inactive state until communication with a mobile device is established. In one example, the pill device can include sensors, such as a pH sensor configured to detect a pH value that activates the pH sensor 404 and causes the pill device to broadcast a signal (e.g., a BLE signal) 406. A mobile device within detection proximity of the signal may detect the signal being broadcast by the pill device and pair with the mobile device 408. For example, the patient device may establish a network connection with the pill device by pairing with the pill device (e.g., via BLUETOOTH pairing). As part of the pairing process, the pill device may send the pill authenticator to the mobile device, and the pill authenticator may be used as a pairing code or passkey. In the case that authentication fails, then the pill device will remain in an inactive state and the active agent contained in the pill device will not be released 412 (i.e., the pill device will pass through the GI tract intact).

In the case that the pill authenticator is able to be authenticated by the mobile device 410, a determination may be made whether secondary authentication 416 may be needed in order to activate 414 the pill device. For example, a healthcare provider, via a drug provisioning service, may indicate that additional security procedures (e.g., authentication questions, PIN number, password, pattern, etc.) are needed prior to activating the pill device to release an active agent 420. Accordingly, the mobile device may be configured to query the drug provisioning service to determine whether additional security procedures are needed. In one example, a healthcare provider may provide prescription instructions for releasing an active agent contained in the pill device. After successful completion of authentication, and any secondary authentication 416, the mobile device may obtain prescription instructions 418 from the drug provisioning service and send the prescription instructions to the pill device 422. The pill device then can use the prescription instructions to release the active agent 420.

Figure 5:
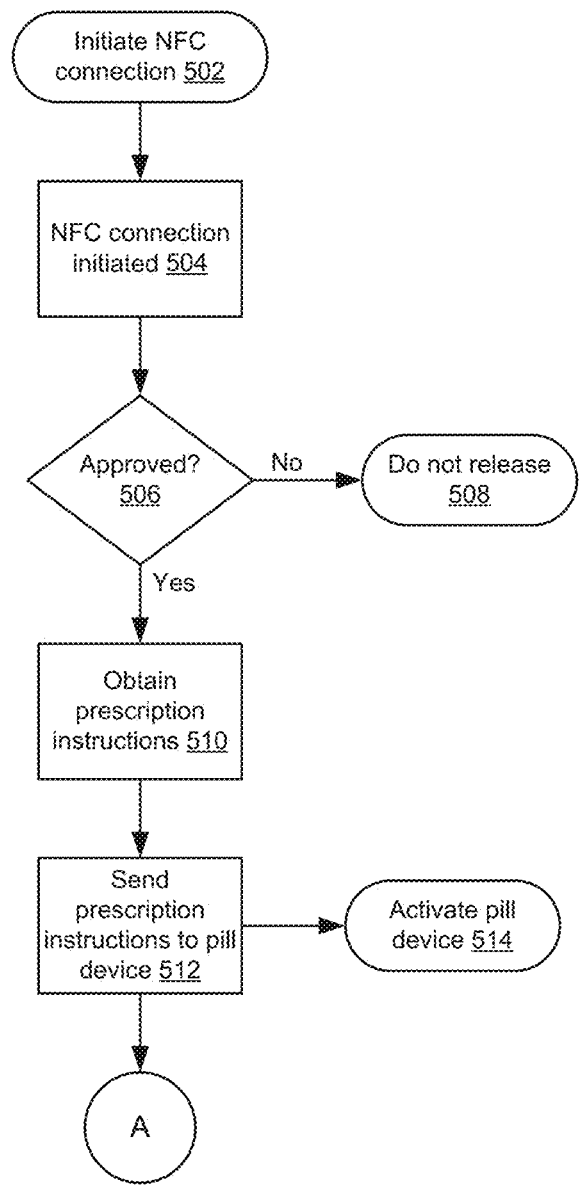
FIG. 5 is a flow diagram illustrating an example method for activating a pill device prior to ingestion.

FIG. 5 is a flow diagram illustrating an example method for activating a pill device prior to ingestion. In this example, a patient prescribed a pill device may activate the pill device using a patient device (e.g., mobile device or implantable device) configured to connect to the pill device using a short-range communication protocol, such as NFC. The method may include initiating a NFC connection 502 with the pill device by placing the patient device in detection proximity of the pill device (e.g., perform an NFC tap). After an NFC connection has been initiated 504, an identification and authentication process can be performed to determine whether the patient has been approved 506 (e.g., prescribed) to take an active agent contained in the pill device. In one example, the identification and authentication process may be performed by a drug provisioning service. For example, a patient identifier stored on a memory device included in the pill device can be retrieved by executing an NFC read using the patient device. The patient device can send the patient identifier obtained from the pill device to the drug provisioning service and the drug provisioning service can verify that the patient identifier is valid and that the pill device has been provisioned to the patient. In the case that the drug provisioning service is unable to identify and authenticate the patient, the pill device is not activated to release 508 the active agent.

In determining that the patient is approved 506 to take the active agent contained in the pill device, the drug provisioning service may obtain prescription instructions 510 for delivering the active agent. Illustratively, the prescription instructions may specify a condition precedent for releasing an active agent, such as, a pH value range to detect in order to release an active agent, a body temperature range to detect in order to release an active agent, a dosing schedule, or a combination of conditions. After obtaining the prescription instructions, the drug provisioning service sends the prescription instructions to the patient device. The prescription instructions can then be transferred to the pill device 512 using a NFC connection, which sends the prescription instructions to the pill device and activates the pill device 514, placing the pill device in condition to release the active agent after ingestion of the pill device by the patient. Having activated the pill device, the patient can now take the pill device and the active agent contained in the pill device can be released according to the prescription instructions, as in the example described below.

Figure 6:
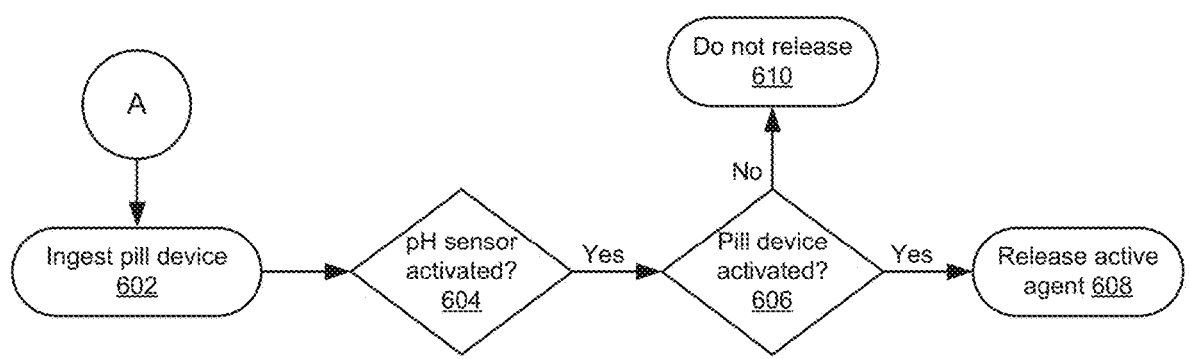
FIG. 6 is a flow diagram that illustrates an example method for releasing an active agent contained in a pill device that has been activated using the activation method in FIG. 5.

FIG. 6 is a flow diagram that illustrates an example method for releasing an active agent contained in a pill device that has been activated using the activation method described above. After activating the pill device, a patient can ingest the pill device 602. In this example, the pill device may include a pH sensor configured to detect a pH specified in prescription instructions stored to the pill device. In the event that the pH sensor detects the pH specified in the prescription instructions 604, and the pill device has been activated 606 as described above, then the pill device may release the active agent 608 contained in the pill device. However, in the event that the pill device has not been activated, the pill device will not release the active agent 610.

Figure 7:
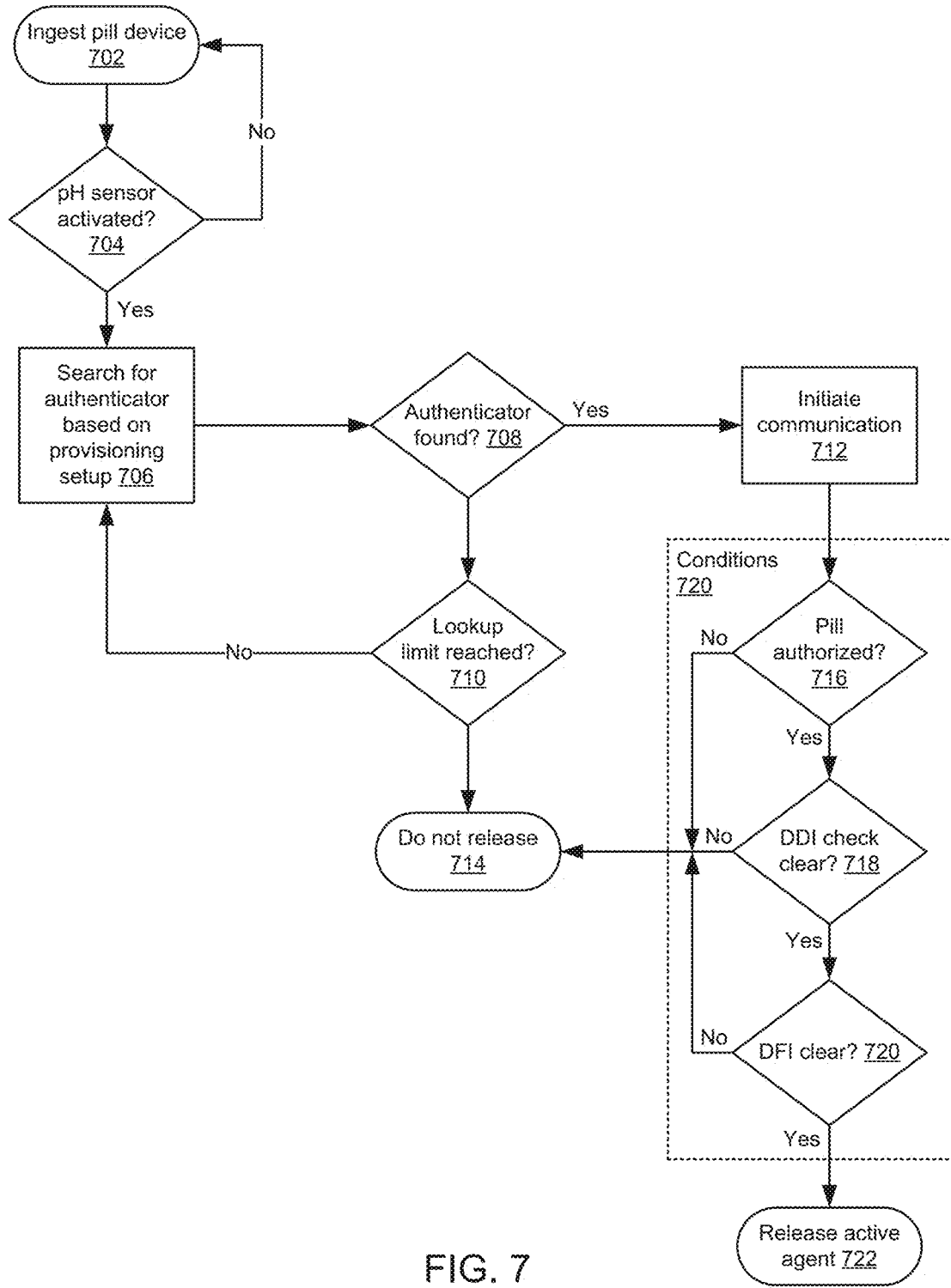
FIG. 7 is a flow diagram illustrating an example method for identifying drug and/or food interactions prior to releasing an active agent using a pill device.

FIG. 7 is a flow diagram illustrating an example method for identifying drug and/or food interactions prior to releasing an active agent using a pill device. As described in association with FIG. 3, a pill device ingested 702 by a patient can include a pH sensor used to detect a pH that activates 704 the pill device. After activating the pill device, a patient device (e.g., a mobile device or an implantable device) may detect a signal sent by the pill device and search for an authenticator (the patient identifier) based on a provisioning setup 706 which stores the patient identifier in a memory of the implantable device.

In the case that the authenticator cannot be found 708 and a lookup limit has been reached 710, the pill device will not release 714 an active agent contained in the pill device. However, in the case that the authenticator (patient identifier) is found 708, then communication can be initiated 712 between the patient device and the pill device and a series of condition precedents 720 to releasing the active agent can be evaluated. As illustrated, a determination may be made whether the pill has been authorized 716 via the authentication process performed above, whether drug-to-drug interactions (DDI) have been checked and are clear 718, and/or whether drug-to-food interactions have been checked and are clear 720. In the case that the conditions precedent are fulfilled, then the pill device may release the active agent 722 contained in the pill device.

Figure 8:
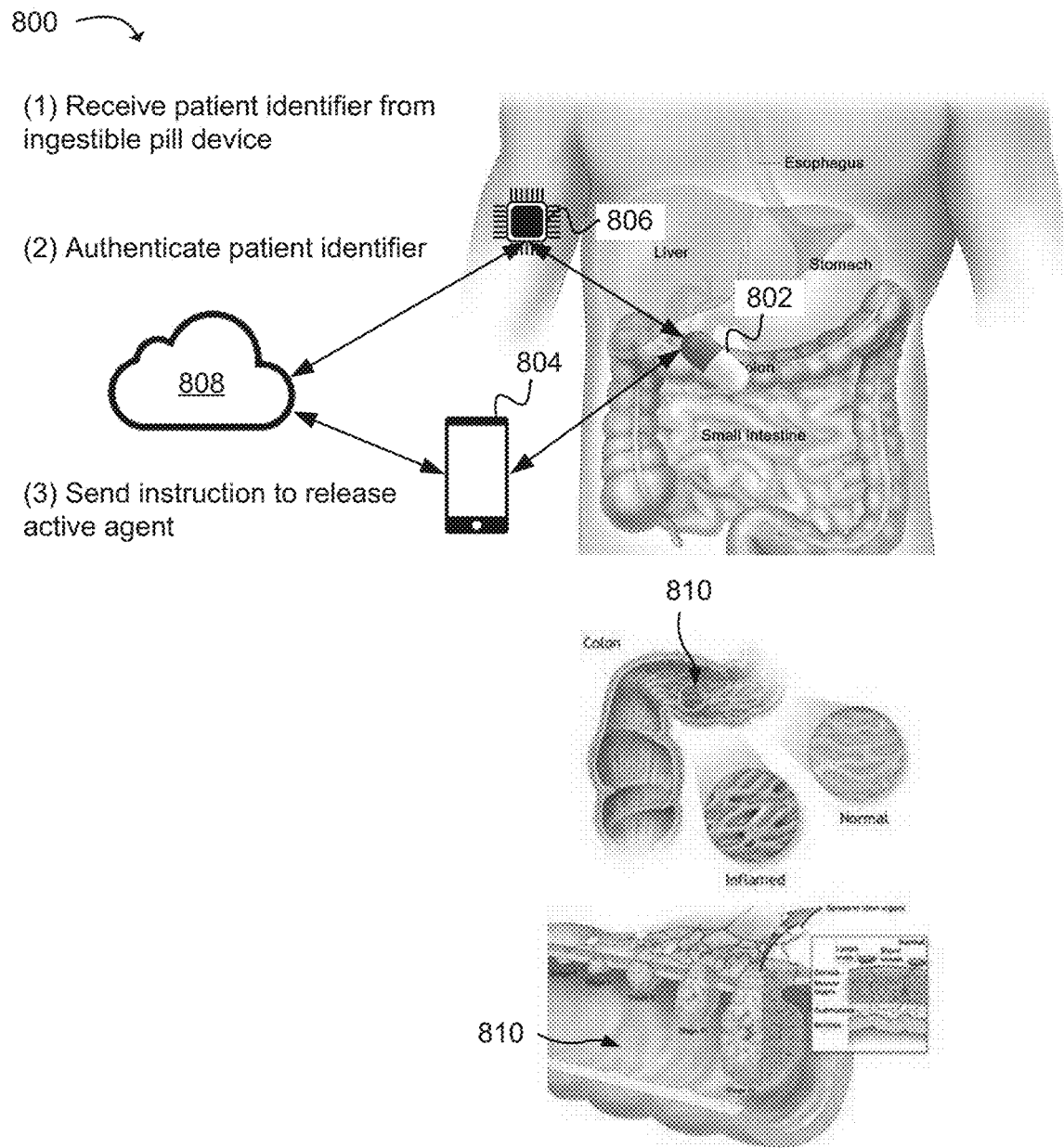
FIG. 8 is a diagram illustrating a high level example of a system for identifying an active agent release point located in a gastrointestinal tract, and releasing an active agent contained in a pill device at the active agent release point.

In one example, the ingestible pill device can be configured with a camera or other optical sensors used to capture images or properties of a gastrointestinal GI tract and sensors to measure GI tract conditions as the pill device travels through the GI tract to identify a release point in the GI tract and release an active agent contained in the pill device. FIG. 8 is a diagram illustrating a high level example of a system 800 for identifying an active agent release point located in a gastrointestinal tract, and releasing an active agent contained in a pill device 802 at the active agent release point. As illustrated, the system 800 can include a pill device 802, which may be configured with one or more sensors used to identify an active agent release point located in a gastrointestinal tract 810. An active agent release point 810 may be one or more locations in a GI tract containing an anomaly associated with a GI tract condition, such as inflammation, ulcerative colitis, irritable bowel syndrome, and other diseases and conditions. The pill device 802 may include a camera incorporated into the pill device 802. The camera may include one or more optical sensors, such as an image sensor, an infrared sensor, and the like. GI images can be captured using the camera and the GI images can be analyzed to identify an active agent release point 802. In one example, a pill device 802 can include a microcontroller configured to analyze GI images and identify an active agent release point represented in a GI image. In another example, the pill device 802 may be configured to wirelessly communicate with a patient device 804/806, such as a mobile device 804 and/or an implantable device 806, which may be configured to analyze GI images received from the pill device and identify an active agent release point represented in a GI image. In yet another example, the patient device 804/806 may forward GI images received from the pill device 802 to an image analysis service hosted in a computing environment 808 (e.g., "cloud" services) configured to analyze the GI images and identify an active agent release point represented in a GI image.

A pill device 802 may contain an active agent prescribed to a patient by a physician. As part of prescribing the active agent to the patient, a drug provisioning service can be used by a healthcare provider to specify an active agent release point 810 and the active agent release point 810 can be obtained from the drug provisioning service by a patient device 804/806 via a computing environment 808. For example, a physician or pharmacist may use the drug provisioning service to provision pill devices 802 to patients and specify an active agent release point 810, as well as dosage instructions, expiration dates, recall requests, etc. used by a pill device 802 to release, or not release, an active agent contained in the pill device. In another example, a pill device 802 can be preconfigured to identify an active agent release point 810 based on GI tract conditions that can be detected using the pill device 802. For example, release parameters can be stored to a memory device included in a pill device 802 at the time of manufacture, or sometime later by a healthcare provider using a RFID or NFC writer.

After being ingested, the pill device 802 may monitor GI tract conditions using GI images captured by a camera and/or sensor data provided by other sensors included in the pill device 802. The GI images and sensor data can be captured at set intervals determined by a healthcare provider, manufacturer, or other entity. As described above, the pill device 802 may be configured to analyze the GI images and/or sensor data to identify an active agent release point 810, or a patient device 804/806 and/or an image analysis service hosted in a computing environment 808 may be configured to analyze the GI images and/or sensor data to identify an active agent release point 810. As an example, the pill device 802 may send GI images, a pH, and a body temperature to an analysis service configured to recognize GI tract anomalies (e.g., inflammation, ulcer, etc.) using image recognition, as well as using the pH and body temperature. In response to identifying a GI tract anomaly, the pill device 802 can be instructed to release an active agent according to dosing instructions that, for example, release the active agent in a single GI tract location, or release the active agent in multiple GI tract locations based on GI images, elapsed time intervals, pH data, temperature data, as well as other conditions.

In one example, a patient profile can be used to release an active agent in a patient GI tract. The patient profile may include information about the patient (e.g., age, gender, conditions, sensitivities, etc.) and the patient profile can be used to modify administration of one or more active agents contained in a pill device 802. For example, based on a patient profile, an amount and/or combination of active agents contained in reservoirs of a pill device 802 may be released to deliver a customized drug dosage to a patient.

After identifying an active agent release point 810 and releasing an active agent, the pill device 802 can capture GI images and/or sensor data and send the GI images and/or sensor data to, for example, a patient device 804 confirming that the active agent was released at the release point 810. An analysis service hosted on the patient device 804 or in computing environment 808 may analyze the GI images and/or sensor data to confirm that the active agent was released at the release point 810.

Figure 9:
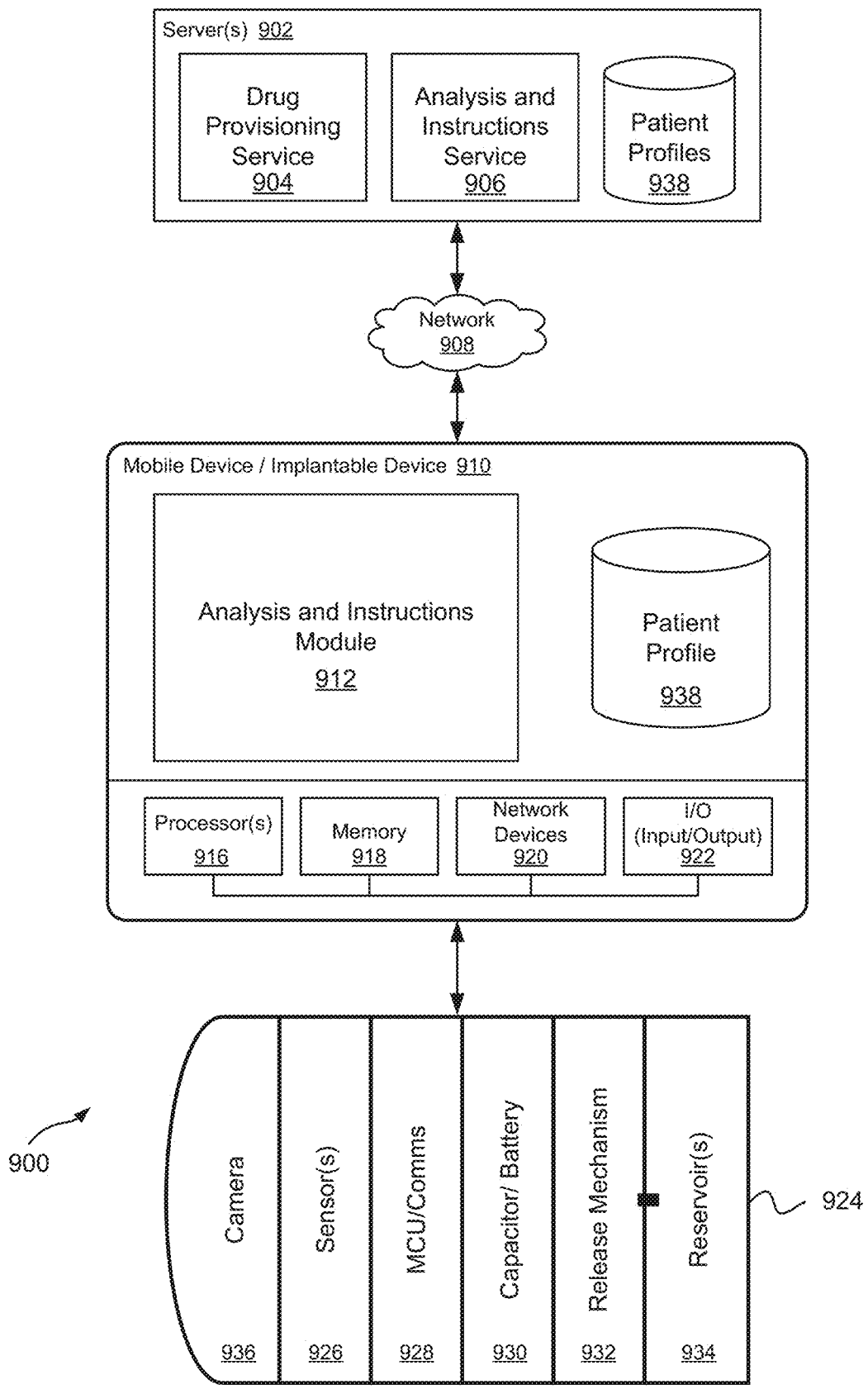
FIG. 9 is a block diagram illustrating components of an example system for delivering an active agent using a pill device.

FIG. 9 illustrates components of an example system 900 for delivering an active agent using a pill device 924. The pill device 924 may be configured to release an active agent after identifying an active agent release point. As illustrated, the pill device 924 can include a camera 936 and sensors 926 that can be used to capture GI tract environment conditions used to identify an active agent release point. In one example, the sensors 926 can include a pH sensor, a temperature sensor, a GPS (Global Positioning System) sensor (used to verify a patient location), and other sensors. The pill device 924 can include a MCU (Microcontroller Unit) and a communication module 928 used to analyze GI images and sensor data for GI conditions associated with an active agent release point, as well as connect to, and communicate with, a patient device 910 (e.g., a mobile device or implantable device). In one example, the MCU may include a machine learning model (e.g., machine learning chip) used to evaluate GI images and identify an active agent release point. The MCU may include a transceiver used to communicate with the patient device 910 using a short-range communication protocol, such as, but not limited to: BLUETOOTH, BLE (Bluetooth Low Energy), ZigBee, Z-Wave, NFC (Near Field Communication), RFID (Radio Frequency Identification), and other short-range communication protocols. Communications between the pill device 924 and the patient device 910 may be associated with the identification and authentication process, and to execute release instructions that activate a release mechanism 932 and release an active agent contained in a one or more reservoirs 934 of the pill device 924. Also, the pill device 924 can include a capacitor or battery 930 used to power the components of the pill device 924.

The patient device 910 can include an analysis and instructions module 912 configured to analyze GI images and/or other sensor data received from the pill device 924 to identify an active agent release point. For example, the pill device 924 may periodically (e.g., every few seconds, minutes, hours, etc.) send GI images and sensor data to the patient device 910 via a short-range communications protocol, and the GI images and sensor data can be provided to the analysis and instructions module 912. Analysis tools, such as image recognition and machine learning can be used to analyze GI images for physical attributes associated with GI conditions that mark an active release point. In the case that GI conditions associated with an active agent release point are identified, the analysis and instructions module 912 may send an instruction to the pill device 924 to release an active agent. In one example, the instruction can include dosing instructions specifying an amount of active agent to release, a combination of active agents to release, and/or a time interval over which to release one or more active agents. The analysis and instructions module 912 may obtain the dosing instructions from a patient profile 938 stored on the patient device 910, or from a drug provisioning service 904 hosted on a server 902 in a computing environment (e.g., "cloud" services). In response to receiving the instructions from the analysis and instructions module 912, the pill device 924 releases the active agent according to the instructions by activating a release mechanism 932 which ejects the active agent from a reservoir 934.

In one example, a patient device 910 may receive GI images and/or sensor data from the pill device 924 and forward the GI images and/or sensor data to an analysis and instructions service 906 hosted on the server 902 in the computing environment. In another example, the pill device 924 may be in network connection with the analysis and instructions service 906 via a wireless network (e.g., WI-FI or cellular network). The analysis and instructions service 906 may be configured to analyze the GI images and/or sensor data using analysis tools, such as image recognition and machine learning, to identify physical attributes associated with GI conditions that mark an active release point. In the case that GI conditions associated with an active agent release point are identified, the analysis and instructions service 906 may send instructions to release an active agent to the pill device 924 (e.g., via the patient device 910 or directly via a wireless network). In one example, the instructions can include dosing instructions obtained from the drug provisioning service 904. After receiving the instructions, the pill device 924 may release the active agent by activating a release mechanism 232, which ejects the active agent from a reservoir 234 included in the pill device 924.

The drug provisioning service 904 hosted on the server 902 in a computing environment may provide a dosing schedule and/or dosing instructions to the pill device 924, via the patient device 910 or directly via a wireless network. The dosing schedule and/or dosing instructions can be obtained from a patient profile 938 containing a patient prescription. Patient profiles 938 may be stored in one or more data stores on a patient device 910 and/or a server 902. The term "data store" may refer to any device or combination of devices capable of storing, accessing, organizing and/or retrieving data, which may include any combination and number of data servers, relational databases, object oriented databases, cluster storage systems, data storage devices, data warehouses, flat files and data storage configuration in any centralized, distributed, or clustered environment. The storage system components of the data store may include storage systems such as a SAN (Storage Area Network), cloud storage network, volatile or non-volatile RAM, optical media, or hard-drive type media. The data store may be representative of a plurality of data stores as can be appreciated.

API calls, procedure calls or other network commands that may be made in relation to the modules and services included in the system 900 may be implemented according to different technologies, including, but not limited to, Representational state transfer (REST) technology or Simple Object Access Protocol (SOAP) technology. REST is an architectural style for distributed hypermedia systems. A RESTful API (which may also be referred to as a RESTful web service) is a web service API implemented using HTTP and REST technology. SOAP is a protocol for exchanging information in the context of Web-based services.

A network 908 used by a device 910 to communicate with the server(s) 902 may include any useful computing network, including an intranet, the Internet, a local area network, a wide area network, a wireless data network, or any other such network or combination thereof. Components utilized for such a system may depend at least in part upon the type of network and/or environment selected. Communication over the network may be enabled by wired or wireless connections and combinations thereof.

FIG. 9 illustrates that certain processing modules may be discussed in connection with this technology and these processing modules may be implemented as computing services. In one example configuration, a module may be considered a service with one or more processes executing on a server or other computer hardware. Such services may be centrally hosted functionality or a service application that may receive requests and provide output to other services or consumer devices. For example, modules providing services may be considered on-demand computing that are hosted in a server, virtualized service environment, grid or cluster computing system. An API may be provided for each module to enable a second module to send requests to and receive output from the first module. While FIG. 9 illustrates an example of a system that may implement the techniques above, many other similar or different environments are possible. The example environments discussed and illustrated above are merely representative and not limiting.

Figure 10:
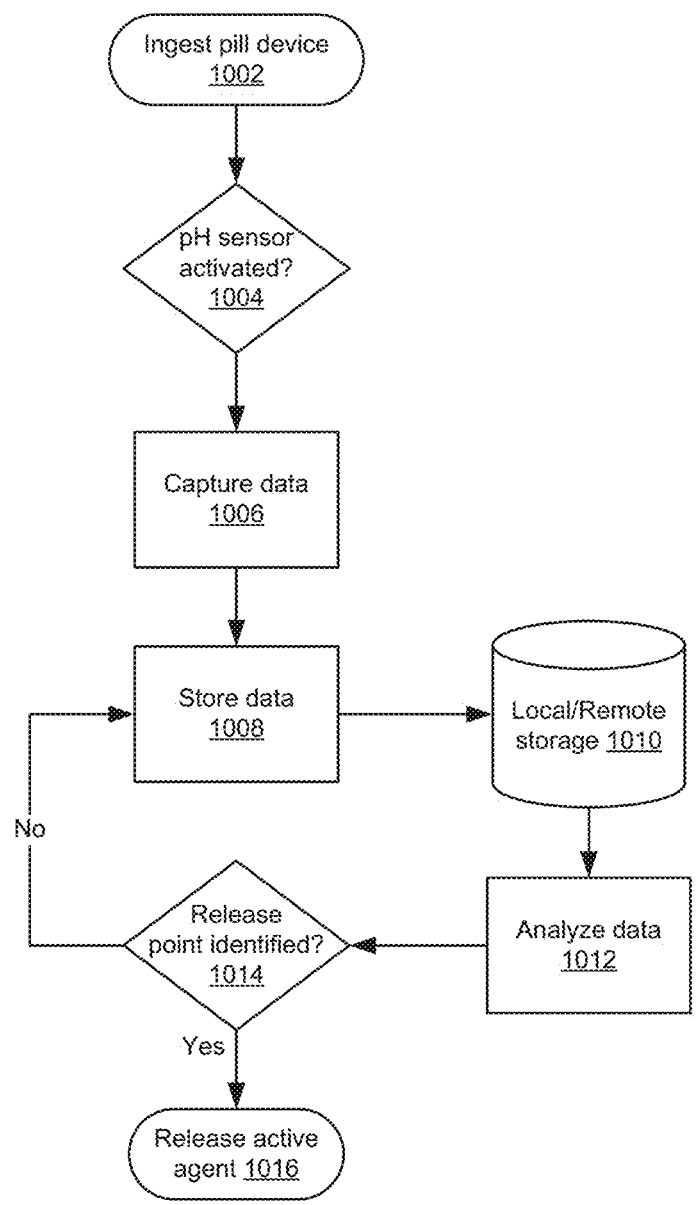
FIG. 10 is a flow diagram illustrating an example method for releasing an active agent to an active agent release point using a pill device.

FIG. 10 is a flow diagram illustrating an example method for releasing an active agent to an active agent release point using a pill device. As part of provisioning a pill device, a healthcare provider may specify one or more release points in a patient's GI tract where an active agent is to be released. A release point may be an anomaly associated with a GI tract condition or disease which can be identified using a GI image and/or sensor data (e.g., pH, temperature, etc.). A healthcare provider can send information for an active agent release point to a pill device (e.g., using an NFC or RFID writer to store the information on a non-volatile memory), a patient device (e.g., a mobile device or implantable device), or to a drug provisioning service used to provide dosing instructions to a pill device or patient device.

As illustrated, a patient can ingest a pill device 1002 provisioned by a healthcare provider. When ingested, the pill device may be in an inactive state and may be activated after detecting a condition. For example, the pill device can include a pH sensor configured to detect a pH value that activates the pH sensor 1004 and causes the pill device to start capturing data 1006. The pill device may begin capturing images of the patient's GI tract using a camera incorporated into the pill device, as well as sensor data (e.g., pH and temperature data) using sensors included in the pill device. The data may be stored 1008, for example, in a local or remote storage 1010. For example, the pill device may be configured to store the data in a storage device contained in the pill device, or the pill device may be configured to send the data via a wireless network to a remote storage, such as a storage contained in a patient device or a storage located in a computing environment (e.g., "cloud" storage).

The data stored to the local or remote storage can be analyzed 1012 to determine whether the data represents the active agent release point. The pill device can be configured to perform the analysis allowing the pill device to act autonomously when the active agent release point is identified, or the analysis can be performed by a remote device or service which can send instructions to the pill device release the active agent when the active agent release point is identified. As an example, an image of a GI tract captured using a pill device camera can be analyzed using an image recognition tool to determine whether the image contains attributes associated with an anomaly or disease. Also, sensor data can be analyzed to determine whether the sensor data (e.g., a pH) corresponds to an anomaly or disease. Moreover, both a GI image and sensor data captured at a GI location can be analyzed to identify the existence of an anomaly or disease at the GI location. For example, an image that shows attributes of ulcerative colitis, along with a pH that corresponds to ulcerative colitis can be used to identify a GI location containing symptoms of ulcerative colitis. In the event that an active agent release point is identified 1014 via analysis of the data captured by the pill device, the active agent may be released 1016. For example, one or more active agent payloads carried by the pill device can be released at the active agent release point.

Figure 11:
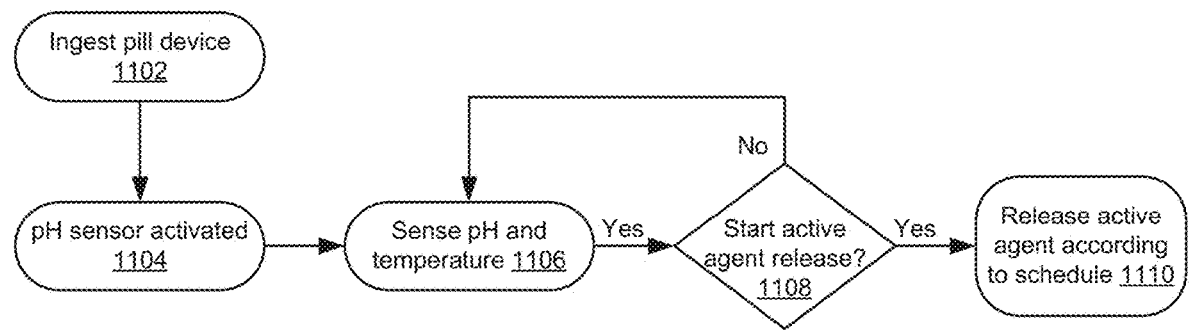
FIG. 11 is a flow diagram that illustrates an example method for delivering an active agent using a pill device according to a dosing plan or schedule.

FIG. 11 is a flow diagram that illustrates an example method for delivering an active agent using a pill device according to a dosing plan or schedule. As described above, a pill device can include a pH sensor configured to detect a pH value. The pill device can be ingested 1102 and the pH sensor can be activated 1104 in response to coming into contact with gastric fluid. Once activated, the pH sensor and a temperature sensor can be used to monitor pH and body temperature 1106 as the pill device advances along the GI tract. The pH and temperature can be monitored for a pH and body temperature occurrence that is associated with an active agent release point. As described earlier, pH and temperature data can also be evaluated along with GI image analysis in order to identify an active agent release point.

In the event that the pH and temperature occurrence linked to the active agent release point is detected, the release of the active agent can be started 1108 and the active agent can be released according to an active agent dosing plan or schedule 1110. Illustratively, a dosing plan or schedule can specify an amount of an active agent (or multiple active agents) to release, an amount of time to continuously release an active agent, and/or a series of release intervals or release events (e.g., subsequent occurrences of an anomaly or disease) to release an active agent. The pill device can be preconfigured to release an active agent according to a dosing plan, or the dosing plan can be sent to the pill device, via a wireless connection, after the pill device has been activated, or after the release point has been identified.

EXAMPLES

The following examples pertain to specific embodiments and point out specific features, elements, or steps that can be used or otherwise combined in achieving such embodiments.

In one example there is provided a controller for authorizing a release of an active agent using an ingestible pill device, the controller comprising circuitry to process instructions, that when executed:

receive an identifier stored on the ingestible pill device, wherein the identifier is linked to patient information;

authenticate the identifier; and initiate release of the active agent contained in the ingestible pill device when authentication of the identifier is successful.

In one example of the controller, the controller is integrated in the ingestible pill device.

In one example of the controller, the controller is integrated in an authenticator device that includes a transceiver used to communicate with the ingestible pill device.

In one example of the controller, the instructions, when executed, further obtain a patient identifier from a memory device coupled to the controller, wherein the identifier is authenticated when the identifier corresponds to the patient identifier retrieved from the memory device.

In one example of the controller, the instructions, when executed, further obtain prescription instructions, wherein release of the active agent corresponds to the prescription instructions.

In one example of the controller, the instructions, when executed, further:

receive sensor data detected by one or more sensors coupled to the ingestible pill device;

analyze the sensor data to determine whether one or more conditions for releasing the active agent are fulfilled; and authorize release of the active agent when the one or more conditions are fulfilled.

In one example of the controller, the one or more sensors coupled to the ingestible pill device includes a pH sensor configured to generate pH data, and the pH data is analyzed to determine whether the pH data meets a pH condition that allows the active agent to be released.

In one example of the controller, the one or more sensors coupled to the ingestible pill device includes an optical sensor configured to generate optical data, and the optical data is analyzed to identify a physical attribute condition that allows the active agent to be released.

In one example of the controller, the one or more sensors coupled to the ingestible pill device includes a chemical sensor configured to detect a chemical, and the environment data is analyzed to identify a chemical attribute condition that allows the active agent to be released.

In one example of the controller, the one or more sensors coupled to the ingestible pill device includes a temperature sensor configured to generate temperature data, and the temperature data is analyzed to identify a temperature condition that allows the active agent to be released.

In one example of the controller, the instructions, when executed, further:

receive an indication from the ingestible pill device that the active agent was released; and cause a record to be generated indicating that the active agent was released.

In one example there is provided an authenticator device or system for authorizing a release of an active agent using an ingestible pill device, comprising:

at least one processor;

a memory device including instructions that, when executed by the at least one processor, cause the authenticator device to:

receive an identifier transmitted from the ingestible pill device, wherein the identifier is stored on the ingestible pill device;

authenticate the identifier transmitted by the ingestible pill device; and send an instruction to the ingestible pill device to release the active agent contained in the ingestible pill device when authentication of the identifier is successful.

In one example of the authenticator device or system, the instructions, when executed by the at least one processor, cause the authenticator device to further obtain a patient identifier stored on the memory device, wherein the patient identifier is used to authenticate the identifier transmitted by the ingestible pill device by determining whether the identifier transmitted by the ingestible pill device corresponds to the patient identifier.

In one example of the authenticator device or system, the instructions, when executed by the at least one processor, cause the authenticator device to further:

obtain patient credentials; and authenticate the patient credentials, wherein authentication of the identifier received from the ingestible pill device and authentication of the patient credentials allows the instruction to release the active agent to be sent to the ingestible pill device.

In one example of the authenticator device or system, the patient credentials are obtained from a patient via a user interface.

In one example of the authenticator device or system, the patient credentials are authenticated using patient information stored in the memory device.

In one example of the authenticator device or system, the patient credentials are sent to a drug provisioning service configured to authenticate the patient credentials.

In one example of the authenticator device or system, the instructions, when executed by the at least one processor, cause the authenticator device to further:

establish a link with the ingestible pill device using a pairing mechanism;

provide a prompt for an authentication question, password, or PIN (Personal Identification Number); and authenticate the authentication question, password, or PIN.

In one example of the authenticator device or system, the instructions, when executed by the at least one processor, cause the authenticator device to further:

detect a broadcast signal transmitted by the ingestible pill device; and establish a network connection with the ingestible pill device using a pairing process that uses the identifier transmitted by the ingestible pill device as a pairing code, wherein successful pairing using the identifier as the pairing code authenticates the identifier transmitted by the ingestible pill device.

In one example of the authenticator device or system, the instructions, when executed by the at least one processor, cause the authenticator device to further:

obtain an encryption key stored on the memory device; and decrypt the identifier transmitted by the ingestible pill device using the encryption key.

In one example of the authenticator device or system, the instructions, when executed by the at least one processor, cause the authenticator device to further:

receive sensor data from the ingestible pill device detected by one or more sensors coupled to the ingestible pill device;

analyze the sensor data to determine whether one or more conditions for releasing the active agent are fulfilled; and authorize release of the active agent when the one or more conditions are fulfilled.

In one example of the authenticator device or system, the sensor data received from the ingestible pill device includes pH data which is analyzed to determine whether the pH data meets a pH threshold condition that allows the instruction to release the active agent to be sent to the ingestible pill device.

In one example of the authenticator device or system, the sensor data received from the ingestible pill device includes optical sensor data which is analyzed to identify a physical attribute condition that allows the instruction to release the active agent to be sent to the ingestible pill device.

In one example of the authenticator device or system, the instructions, when executed by the at least one processor, cause the authenticator device to further:

receive a gastrointestinal (GI) image from the ingestible pill device;

analyze the GI image to identify an active agent release point located in a GI tract; and determine that the GI image represents an active agent release point that allows the instruction to release the active agent to be sent to the ingestible pill device.

In one example of the authenticator device or system, the sensor data received from the ingestible pill device includes chemical sensor data which is analyzed to identify a chemical attribute condition that allows the instruction to release the active agent to be sent to the ingestible pill device.

In one example of the authenticator device or system, the instructions, when executed by the at least one processor, cause the authenticator device to further:

obtain dosing instructions from a patient prescription service via a network; and send the dosing instructions to the ingestible pill device to enable the ingestible pill device to release the active agent according to the dosing instructions.

In one example of the authenticator device or system, the instruction to release the active agent contained in the ingestible pill device are sent at staged intervals according to the dosing instructions, wherein the ingestible pill device is configured to release a defined amount of the active agent during each staged interval.

In one example of the authenticator device or system, the dosing instructions specify an amount of the active agent to release.

In one example of the authenticator device or system, the instruction to the ingestible pill device to release the active agent activates the ingestible pill device prior to ingestion of the ingestible pill device and the ingestible pill device releases the active agent after detecting a condition for releasing the active agent using a sensor.

In one example of the authenticator device or system, the ingestible pill device is activated prior to ingestion using a Near Field Communication (NFC) enabled device.

In one example of the authenticator device or system, the instruction to release the active agent contained in the ingestible pill device is not sent to the ingestible pill device when authentication of the identifier fails or when one or more conditions are not fulfilled.

In one example of the authenticator device or system, the instructions, when executed by the at least one processor, cause the authenticator device to further:

receive an indication from the ingestible pill device that the active agent was released; and cause a record to be generated indicating that the active agent was released.

In one example of the authenticator device or system, the authenticator device or system further comprises a short-range communication device configured to use a short-range communications protocol to communicate with the ingestible pill device.

In one example of the authenticator device or system, the authenticator device or system further comprises a networking device configured to connect to a data network used to communicate with the ingestible pill device.

In one example of the authenticator device, the authenticator device is a subdermal implantable device that includes a transceiver used to communicate with the ingestible pill device.

In one example of the authenticator device, the authenticator device is a mobile device configured to communicate with the ingestible pill device.

In one example there is provided an ingestible pill device for delivering an active agent, comprising:

a pill housing including a reservoir configured to contain the active agent;

a release mechanism configured to release the active agent contained in the reservoir into a GI (gastrointestinal) tract; and a controller including circuitry to process instructions, that when executed:

initiate authentication of an identifier stored on the ingestible pill device; and initiate release of the active agent contained in the ingestible pill device when authentication of the identifier is successful.

In one example of the ingestible pill device, the ingestible pill device further comprises a transceiver used to transmit the identifier to an authenticator device configured to authenticate the identifier and provide release instructions to the ingestible pill device for releasing the active agent.

In one example of the ingestible pill device, the instructions, when executed by the controller, further receive dosing instructions for the active agent and release the active agent according to dosing instructions.

In one example of the ingestible pill device, the instructions, when executed by the controller, further release the active agent at staged intervals according to dosing instructions, resulting in releasing a defined amount of the active agent during each staged interval.

In one example of the ingestible pill device, the ingestible pill device further comprises at least one sensor configured to generate sensor data used to determine whether one or more conditions for releasing the active agent are fulfilled.

In one example of the ingestible pill device, the at least one sensor includes a camera configured to capture a GI image, and the instructions, when executed by the controller, further analyze the GI image to identify an active agent release point located in the GI tract and determine that the GI image represents an active agent release point that allows for the release of the active agent.

In one example of the ingestible pill device, the at least one sensor includes a pH sensor configured to generate pH data, and the instructions, when executed by the controller, further;

analyze the pH data to identify an active agent release point located in the GI tract; and determine that the pH data corresponds to the active agent release point that allows for the release of the active agent.

In one example of the ingestible pill device, the at least one sensor includes a temperature sensor, and the instructions, when executed by the controller, further analyze temperature data generated by the temperature sensor to detect a body temperature value in the GI tract that corresponds to an active agent release point located in the GI tract that allows for the release of the active agent.

In one example of the ingestible pill device, the instructions, when executed by the controller, further:

send the sensor data to an analysis service configured to analyze the sensor data and identify an active agent release point located in the GI tract; and receive an instruction from the analysis service to release the active agent contained in the ingestible pill device.

In one example of the ingestible pill device, wherein the controller includes an MCU (Microcontroller Unit) configured to execute a machine learning model used to analyze the sensor data and determine a condition that allows the release the active agent.

In one example of the ingestible pill device, the instructions, when executed by the controller, further transmit a notification indicating that the active agent was released.

In one example there is provided, a computer implemented method for delivering an active agent using an ingestible pill device, comprising:

capturing a GI (gastrointestinal) image using a camera incorporated into the ingestible pill device;

analyzing the GI image to identify an active agent release point located in a gastrointestinal tract;

determining that the GI image represents the active agent release point; and releasing the active agent contained in the ingestible pill device to deliver the active agent to the release point located in the gastrointestinal tract In one example of the method for delivering an active agent using an ingestible pill device, the method further comprises detecting a pH value in the gastrointestinal tract that corresponds to the active agent release point located in a gastrointestinal tract, wherein the pH value and the GI image are used to identify the active agent release point in the gastrointestinal tract.

In one example of the method for delivering an active agent using an ingestible pill device, the method further comprises detecting a body temperature value in the gastrointestinal tract that corresponds to the active agent release point located in a gastrointestinal tract, wherein the body temperature value and the GI image are used to identify the active agent release point in the gastrointestinal tract.

In one example of the method delivering an active agent using an ingestible pill device, analyzing the GI image further comprises analyzing the GI image using a MCU (Microcontroller Unit) and a machine learning model incorporated into the ingestible pill device.

In one example of the method delivering an active agent using an ingestible pill device, identifying the active agent release point further comprises:

sending the GI image to an image analysis service configured to analyze the GI image to identify the active agent release point located in the gastrointestinal tract; and receiving an instruction to release the active agent contained in the ingestible pill device.

In one example there is provided, an ingestible pill device for delivering an active agent, comprising:

a pill housing including a reservoir configured to contain the active agent;

a release mechanism configured to release the active agent contained in the active agent reservoir into a gastrointestinal tract; and a memory device including instructions that, when executed by at least one processor, cause the ingestible pill device to:

receive a GI (Gastrointestinal) image transmitted from a camera;

analyze the GI image to identify an active agent release point located in a gastrointestinal tract;

determine that the GI image represents the active agent release point; and release the active agent contained in the ingestible pill device.

In one example there is provided, system for delivering an active agent using an ingestible pill device, comprising:

at least one processor;

a memory device including instructions that, when executed by the at least one processor, cause the system to:

receive a GI (Gastrointestinal) image transmitted from the ingestible pill device via a short-range communications protocol, wherein the ingestible pill device includes a camera and transceiver used to transmit the GI image;

analyze the GI image received from the ingestible pill device to identify an active agent release point located in a gastrointestinal tract;

determine that the GI image received from the ingestible pill device represents the active agent release point; and send an instruction to the ingestible pill device via the short-range communications protocol to release the active agent contained in the ingestible pill device.

In one example of the ingestible pill device or the system for delivering the active agent using the ingestible pill device, the GI image is analyzed to identify a GI condition that is linked to the active agent release point.

In one example of the ingestible pill device or the system for delivering the active agent using the ingestible pill device, the memory device includes instructions to further:

receive a pH value obtained from the GI tract using a pH sensor included in the ingestible pill device; and determine that the pH value corresponds to the active agent release point.

In one example of the ingestible pill device or the system for delivering the active agent using the ingestible pill device, the memory device includes instructions to further:

receive a body temperature value obtained from the GI tract using a temperature sensor included in the ingestible pill device; and determine that the body temperature value corresponds to the active agent release point.

In one example of the ingestible pill device or the system for delivering the active agent using the ingestible pill device, the memory device includes instructions to further identify the active agent release point based on a determination that:

the GI image represents a GI tract location associated with the active agent release point, a pH value corresponds to a pH of the GI tract location associated with the active agent release point, and a body temperature value corresponds to a temperature of the GI tract location associated with the active agent release point.

In one example of the ingestible pill device or the system for delivering the active agent using the ingestible pill device, the memory device includes instructions to further release the active agent at staged intervals according to a dosing schedule, wherein the ingestible pill device is configured to release a defined amount of the active agent during each staged interval.

In one example of the ingestible pill device or the system for delivering the active agent using the ingestible pill device, the memory device includes instructions to further obtain dosing instructions from a patient prescription service which are used to determine one or more GI tract locations to release the active agent contained in the ingestible pill device.

Example Embodiments for Securing and Monitoring Medication Using a Monitoring Device Technology is described for monitoring the contents of a medication compartment or package, such as a blister package, using a monitoring device configured to detect that the content of a medication compartment has been removed. Medication compartment content can be monitored to determine whether a patient is adhering to a medication prescription. Medication adherence refers to whether a patient takes a medication as prescribed. Medication non-adherence is a growing concern for clinicians, pharmaceutical companies, healthcare systems, insurance companies, and governments due to evidence that non-adherence is prevalent and associated with adverse treatment outcomes and higher costs of care.

Medication packaging may have benefits in terms of providing drug authenticity, safety, preservation, and protection of a drug. The present technology can be used to monitor a medication package (e.g., a blister pack) using a monitoring device and detect events (e.g., the removal of a pharmaceutical pill, including tablets, capsules, or variants) that indicate that medication has been removed from the medication package. Detection of these events can be used to determine whether a patient is adhering to a medication prescription. In one example, the monitoring device can be removably attached to a medication package (e.g., an outside edge of a blister package), such that a camera, included in the monitoring device, is oriented to have a field of view of the medication package to detect changes in the medication package. For example, the camera may have a field of view that includes a set of blisters included in a blister package. The monitoring device can be configured to detect when the monitoring device (and a medication package) is handled by way of a change in orientation of the monitoring device using a gyroscope, and capture images of the medication package using the camera. The images can be analyzed (e.g., using a microcontroller included in the device, or by sending the images to a monitoring service) to determine whether, for example, a blister has been deformed, indicating that the content of a blister has been removed. A record can be updated to indicate that the content of a medication compartment (e.g., blister) has been removed, and the record can be used by a monitoring service to track medication adherence to a medication prescription.

Figure 12A:
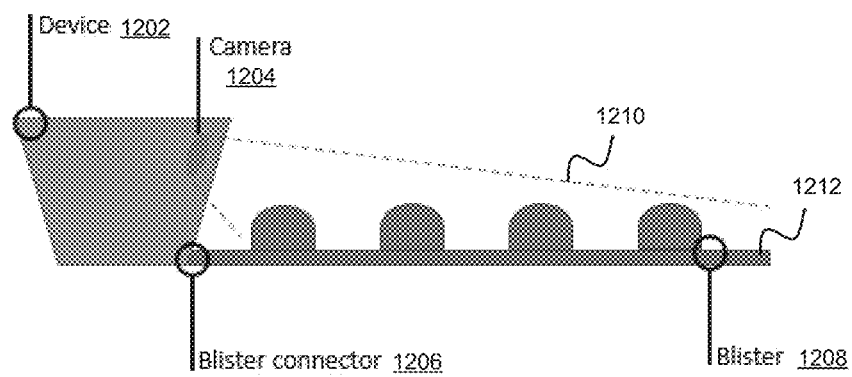
FIGS. 12A-12B illustrate an example monitoring device configured to monitor medication package content to determine whether a patient is adhering to a medication prescription.

To further describe the technology, examples are now provided with reference to the figures. FIG. 12A illustrates an example of a monitoring device 1202 configured to monitor a medication container (e.g., a blister package 1212) to determine whether a patient is adhering to a medication prescription. In one example, information for a prescription issued to a patient can be sent to a package monitoring application installed on a mobile device, or a package monitoring service hosted in a computing environment ("cloud" services). The prescription information can include details for a blister package 1212, containing a pharmaceutical issued to the patient, such as, a blister package configuration (e.g., number and size of blisters 1208), issue date, expiration date, and other prescription information.

Figure 12B:
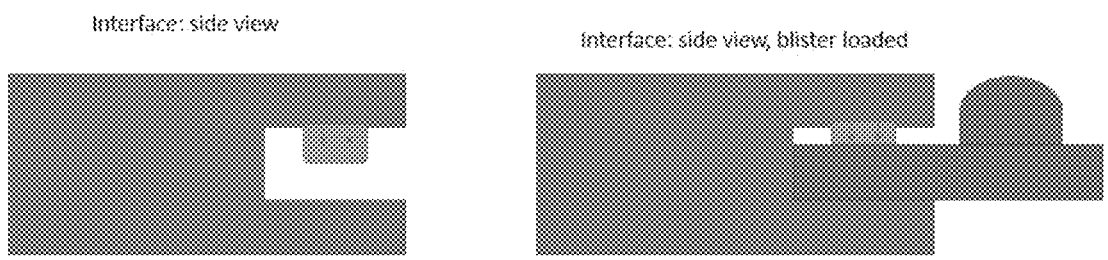

After receiving the prescription information, a patient may receive a message, via the patient's mobile device (e.g., from the package monitoring application or service (not shown) that received the prescription information), requesting that the patient attach the monitoring device 1202 to the blister package 1212. The monitoring device 1202 may be removably attached to the blister package 1212 using a blister connector 1206. For example, the blister connector 1206 may include a clip-on interface that attaches to an edge of a blister package (as shown in FIG. 12B). The patient can attach the monitoring device 1202 to the blister package 1212 using the blister connector 1206, and the monitoring device 1202 can be activated, for example, by a pressure switch in the blister connector 1206, or by a device display or button integrated into the monitoring device 1202, or by a package monitoring application or service configured to communicate with the monitoring device 1202 via a wireless network.

Once activated, the monitoring device 1202 can be calibrated using the prescription information provided to the package monitoring application or service. For example, a blister configuration can be sent to the monitoring device 1202 (or the package monitoring application or service), and the blister configuration can be used to align blisters 1208 identified in the blister package 1212 with the blister configuration provided to the monitoring device 1202 (or the package monitoring application or service). As illustrated, the monitoring device 1202 includes a camera 1204 positioned to have a field of view 1210 of a set of blisters 1208 included in the blister package, or a field of view of a set of blister seals that cover blister cavities containing pharmaceuticals. As part of calibrating the monitoring device 1202, an image captured using the camera 1204 can be analyzed by the monitoring device 1202 (or by the package monitoring application or service) to identify a blister configuration represented in the image compare the image's blister configuration with the prescription information's blister configuration to determine whether the configurations match. Also, the image captured of the blister package may provide an initial image that can be compared with subsequent images to determine an intact state of the blisters 1208. In one example, the camera 1204 may be configured to adjust (e.g., via an aperture or camera actuator) to have a field of view 1210 that includes the blisters of a blister package, and/or the blister connector 1206 may be configured to adjust (move) based on camera feedback to provide the camera 1204 with a field of view 1210 that includes the blisters of a blister package.

After activating and calibrating the monitoring device 1202, the monitoring device 1202 may switch to an inactive state (e.g., standby mode). The monitoring device 1202 may be configured to detect a change in orientation of the monitoring device 1202 (e.g., using gyroscope included in the monitoring device 1202) that causes the monitoring device 1202 to switch to an active state and start monitoring the blisters 1208 of the blister package 1212. For example, picking up the monitoring device 1202 may cause the monitoring device 1202 to switch to an active state.

Monitoring of the blister package 1212 may comprise capturing one or more images of the blister package 1212 and comparing the images to determine whether a blister 1208 has been accessed. As one example, a first image (e.g., the initial image captured during calibration, or a last known image) of the blisters 1208 can be compared with a second image of the blisters 1208 to determine whether any of the blisters 1208 have been deformed. As another example, a first image of blister seals can be compared with a second image of the blister seals to determine whether any of the blister seals have been broken. In the case that a determination is made that a blister 1208 has been accessed, the monitoring device 1202 can record the date and time that the blister 1208 was accessed. The monitoring device 1202 can store the record in memory of the monitoring device 1202, and send the record to the package monitoring application or service. By monitoring the state of the blisters 1208 and/or the blister seals, a determination whether a medication is being dispensed via the blister package according to a medication prescription can be made. Also, the monitoring device 1202 can be configured to preform various functions related to medication prescriptions, such as notifications and alarms associated with dosing instructions, dosing schedules, and unauthorized access to pharmaceuticals.

Figure 13:
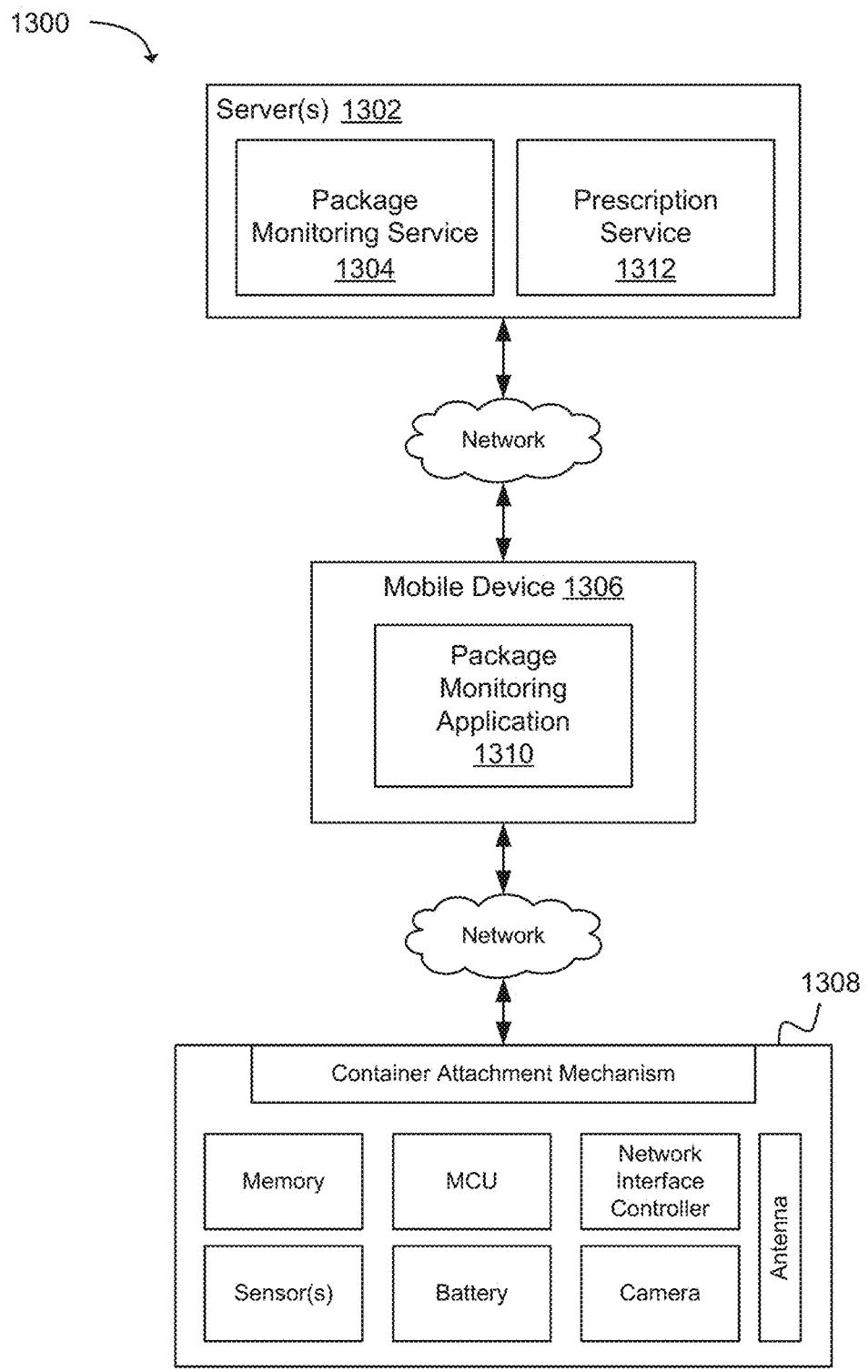
FIG. 13 is a block diagram illustrating components of an example system for monitoring patient compliance to a medication prescription.

FIG. 13 is a block diagram illustrating components of an example system 1300 for monitoring patient compliance to a medication prescription. As illustrated the system 1300 can include a monitoring device 1308 configured to monitor patient access to medication contained in a medication container, a mobile device 1306 configured to execute a package monitoring application 1310, and one or more servers 1302 in a computing environment (e.g., "cloud" services) that host a package monitoring service 1304 and a prescription service 1310.

Figure 14:
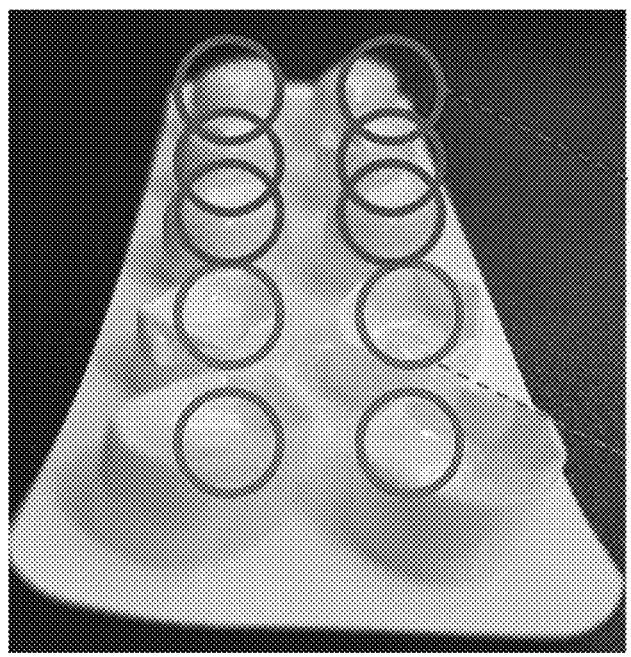
FIG. 14 shows an image of blisters in a blister package that can be analyzed to determine whether a blister is deformed.

The components of the monitoring device 1308 can include, but are not limited to: an MCU (Microcontroller Unit) used to perform functions associated with monitoring a blister package, a camera used to capture images of a medication container, a memory device (e.g., flash memory or PMC) used to store images, records, and/or prescription information, one or more radio devices (e.g., BLE, WI-FI, LTE) and antenna used to communicate with the mobile device 1306 or servers 1302 via a wireless network, and a power source, such as rechargeable battery. Also, the monitoring device 1308 can include sensors, such as a gyroscope and accelerometer used to determine an orientation and movement of the monitoring device 1308, temperature sensor and humidity sensors used to monitor an environment that may have an effect on a pharmaceutical, biosensors used for security and authentication functions. The monitoring device 1308 can include a display used to show a state of the monitoring device 1308 and medication container, and provide prescription and patient information. In one example, the monitoring device 1308 can be configured to analyze images of a medication container. A medication container can include a blister package, a pill container, pill organizer, a bottle, or other container containing a pharmaceutical. For example, the monitoring device 1308 can analyze images of blisters in a blister package in order to determine whether a blister is deformed (as shown in FIG. 14), indicating that the content contained in the blister has been removed, and update a record with a date and time that the blister was accessed. As another example, the monitoring device 1308 can analyze images of a pill container or pill organized to determine whether an individual pill container is empty, indicating that the content of the pill container has been removed, and update a record with a date and time that the pill container was accessed. The monitoring device sends a record to the package monitoring application 1310 or service 1304 (e.g., via BLE or WI-FI), which tracks the content of the blister package to determine patient compliance to a medication prescription.

The mobile device 1306 may be used to execute the package monitoring application 1310, which may be configured to receive a medication container status from the monitoring device 1308 via a short-range communications protocol, such as BLE or WI-FI, which can be used to track the content of the medication container to determine patient adherence to a medication prescription. Also, the package monitoring application 1310 can be configured to analyze images captured by the monitoring device 1308 to determine the status of containers in a medication package and track the content of the containers. For example, the package monitoring application 1310 can analyze images of blisters included in a blister package to determine whether a blister is deformed (as shown in FIG. 14), indicating that the content contained in the blister has been removed. Also the package monitoring application 1310 can forward a medication container status to the package monitoring service 1304 hosted on the servers 1302, allowing a physician to monitor patient adherence to a medication prescription.

The servers 1302 can be used to host the prescription service 1310, which can be configured to receive a prescription issued to a patient and send prescription information to the package monitoring application 1310 installed on a mobile device, or to the package monitoring service 1304 hosted of the severs 1302. The package monitoring service 1304 can be configured to track the content of a medication package to determine patient adherence to a medication prescription. Also, the package monitoring application 1310 can be configured to analyze images captured by the monitoring device 1308 to determine the status of containers in the medication package and track the content of the medication package. As an example, the package monitoring service 1304 can analyze images of blisters included in a blister package to determine whether a blister is deformed (as shown in FIG. 14), indicating that the content contained in the blister has been removed.

API calls, procedure calls or other network commands that may be made in relation to the modules and services included in the system 1300 may be implemented according to different technologies, including, but not limited to, Representational state transfer (REST) technology or Simple Object Access Protocol (SOAP) technology. REST is an architectural style for distributed hypermedia systems. A RESTful API (which may also be referred to as a RESTful web service) is a web service API implemented using HTTP and REST technology. SOAP is a protocol for exchanging information in the context of Web-based services.

A network used by the mobile device 1306 to communicate with the server(s) 1302 can include any useful computing network, including an intranet, the Internet, a local area network, a wide area network, a wireless data network, or any other such network or combination thereof. Components utilized for such a system may depend at least in part upon the type of network and/or environment selected. Communication over the network may be enabled by wired or wireless connections and combinations thereof.

Figure 15:
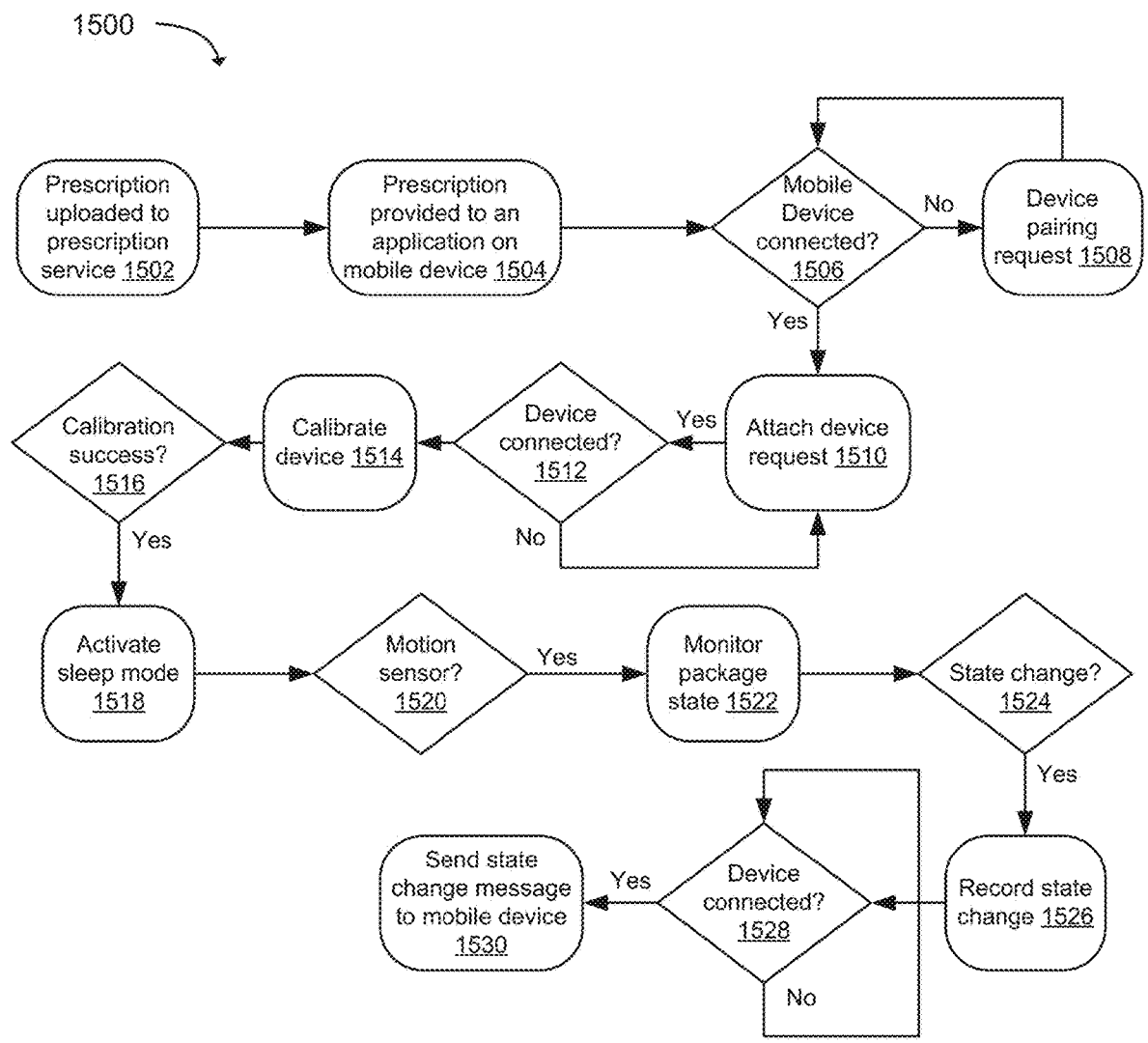
FIG. 15 is a flow diagram illustrating a method for monitoring the state of medication containers included in a medication package.

FIG. 13 illustrates that certain processing modules may be discussed in connection with this technology and these processing modules may be implemented as computing services. In one example configuration, a module may be considered a service with one or more processes executing on a server or other computer hardware. Such services may be centrally hosted functionality or a service application that may receive requests and provide output to other services or consumer devices. For example, modules providing services may be considered on-demand computing that are hosted in a server, virtualized service environment, grid or cluster computing system. An API may be provided for each module to enable a second module to send requests to and receive output from the first module. While FIG. 13 illustrates an example of a system that may implement the techniques above, many other similar or different environ- FIG. 15 is a flow diagram illustrating a method 1500 for monitoring the state of containers in a medication container or package. As in block 1502, a prescription can be uploaded to a prescription service, the prescription can then be provided to an application on a mobile device, as in block 1504. Thereafter, as in block 1506, the application can be configured to determine whether the mobile device is connected to a monitoring device configured to monitor a medication package (e.g., blister package) using a camera to capture images of the medication package and detect access to the containers (e.g., blisters) included in the medication package. In the case that the mobile device is not connected to the monitoring device, as in block 1508, a device pairing request (e.g., BLE pairing request) may be sent to the monitoring device.

As in block 1512, the monitoring device can be configured to detect whether the monitoring device is connected to a medication package. If not already attached, as in block 1510, a request may be sent to the mobile device requesting that a user attach the monitoring device to the medication package. After the monitoring device has been attached to the medication package, then as in block 1514, the monitoring device can be calibrated to the medication package, as described earlier. Having calibrated the monitoring device, then as in block 1518, the monitoring device may be activated and placed in sleep mode to conserve energy. While in sleep mode, the monitoring device may be configured to monitor movement of the monitoring device using a motion sensor. As in block 1520, in response to detecting motion, the monitoring device may begin monitoring the state of the medication package, as in block 1522. As in block 1524, in the case that a container state change is detected (e.g., a determination is made that a blister has been deformed, or a blister seal has been broken), then as in block 1526, the container state change can be recorded to a record. The record can be stored on the monitoring device and can be periodically sent to the mobile device. As such, the monitoring device, as in block 1528, may determine whether the monitoring device is connected to the mobile device, and in the case that the devices are connected, then as in block 1530, the monitoring device may send a message to the mobile device indicating the state change of the medication package.

Figure 16:
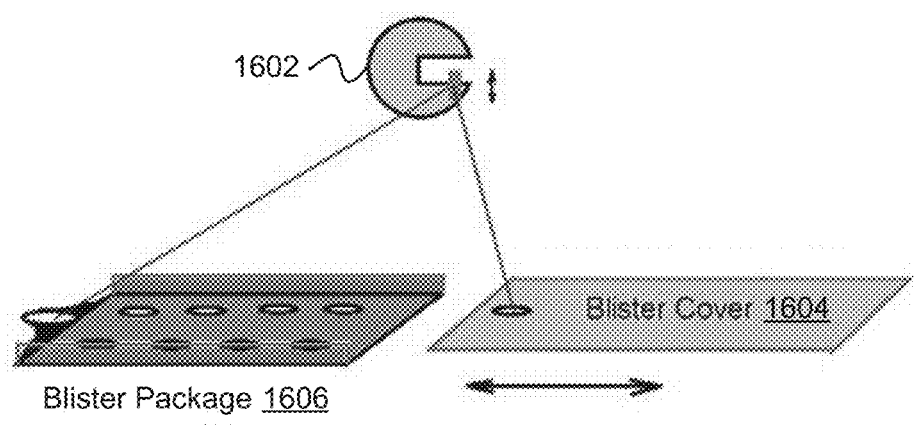
FIG. 16 is a diagram illustrating a blister pack locking device that includes a network connected lock device and a blister pack cover.
Figure 18:
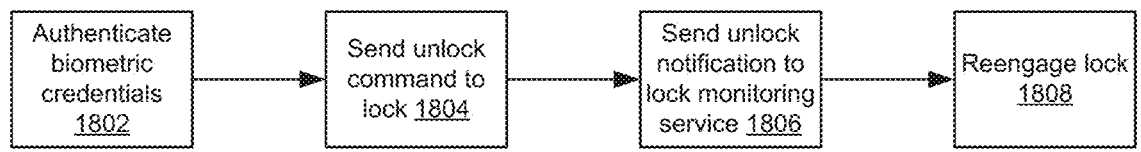
FIG. 18 is a flow diagram illustrating a method for controlling access to a medication package using a locking device.

In one example, as shown in FIG. 16, a locking device can be used to secure a medication package, such as a blister package. The locking device can include a cover and a network connected lock device. The cover can be configured to attach to a medication package and prevent access to containers containing pharmaceuticals. The lock device can be configured to secure the cover to a medication package and the lock device can be controlled via another device over a network. For example, a mobile device can connect to the lock device using a short-range communications protocol (e.g., BLE, NFC, WI-FI, etc.) and the mobile device can be used to send lock and unlock commands to the lock device. In another example, the lock device can be configured to include a biometric sensor which can be used to lock/unlock the lock device. The lock device can be configured to interface with a lock monitoring service hosted in a computing service environment ("cloud" services), which may be configured to monitor access to a medication package via the locking device. In one example, as shown in FIG. 18, a monitoring device configured to monitor access to a medication package may include a cover configured to attach to the medication package and a network connected lock device configured to secure the cover to the medication package to prevent unauthorized access to the medication package.

Referring now to FIG. 16, a diagram illustrates a medication package locking device. In particular, the locking device illustrated is configured to secure a blister package. The locking device includes a network connected lock device 1602 and a blister pack cover 1604. The blister pack cover 1604 can be configured to engage a portion of a blister package 1606 that provides access to blister cavities. For example, the blister pack cover 1604 can comprise a tray portion configured to hold a blister package, and a cover portion configured to slide into the tray portion and cover a face of the blister package 1606 providing access to blister cavities containing a pharmaceutical. The blister pack cover 1604 can include an attachment point where the lock device 1602 can be engaged and locked to the blister pack cover 1604, thereby preventing access to the blister package 1606.

Figure 17:
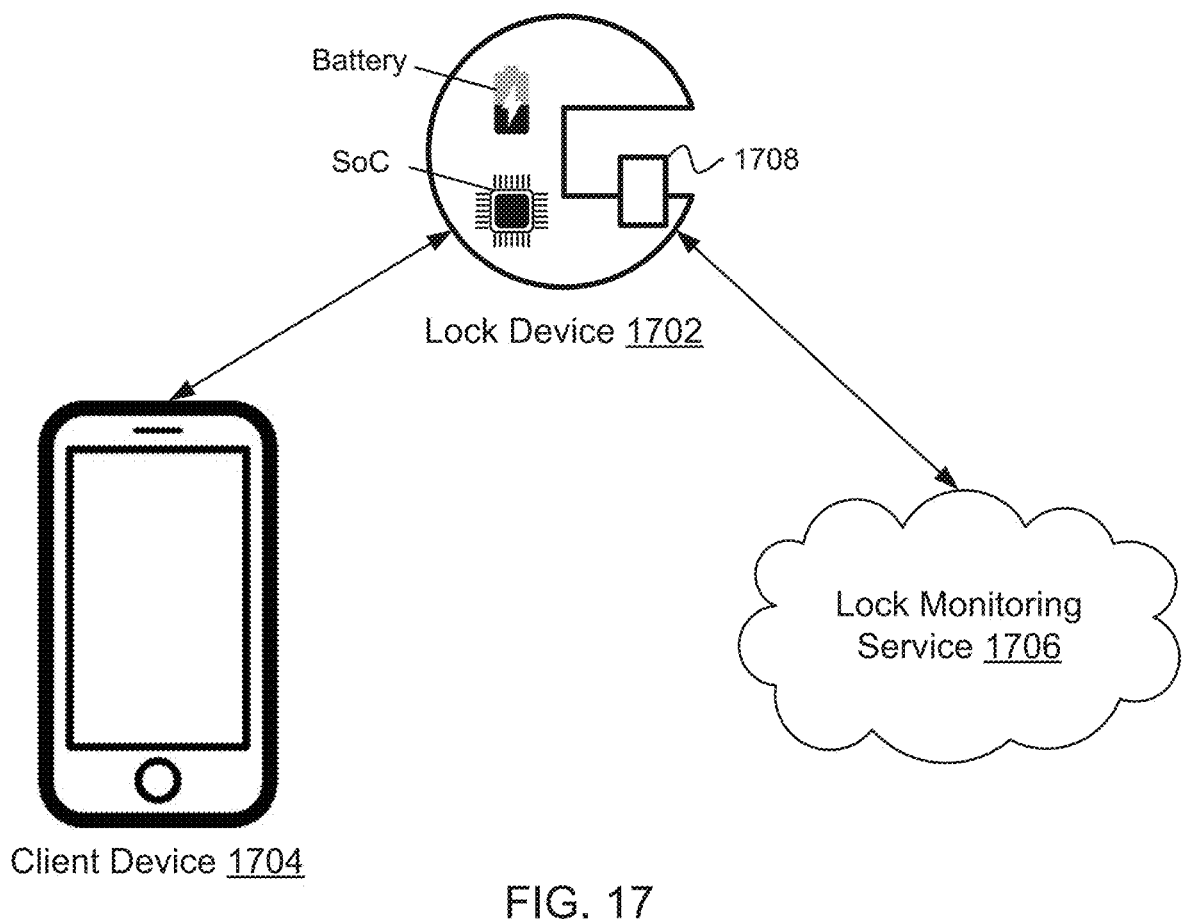
FIG. 17 is a diagram that illustrates and example system for monitoring a locking device.

As shown in FIG. 17, the lock device 1702 can include hardware and software (e.g., a System on a Chip (SoC) that enables the lock device 1702 to be wirelessly connected to a client device 1704 and/or a lock monitoring service 1706. For example, the client device 1704 can be used to control the lock device 1702 by sending lock/unlock commands to the lock device 1702. As an illustration, a patient prescribed a pharmaceutical can use an application installed on the client device 1704 to lock the lock device 1702, securing a cover to a medication package, and unlock the lock device 1702, allowing the cover to be removed from the medication package and allowing access to the content of the medication package. In one example, a client device 1704 may be set (designated) as a trusted device (e.g., a device paired to the lock device 1702). As such, commands received from the client device 1704 may be trusted (e.g., the identity of the client device 1704 may be trusted), and the lock device 1702 executes commands received from the client device 1704 without having to perform additional authentication.

In another example, the lock monitoring service 1706 can be configured to send lock/unlock commands to the lock device 1702. For example, lock/unlock requests can be sent to the lock monitoring service 1706 (via a client device 1704) and the lock monitoring service 1706 can be configured to send lock/unlock commands to the lock device 1702 over a network. Also, the lock monitoring service 1706 can be configured to monitor access to a medication package secured using a locking device. The lock monitoring service 1706 may maintain a record of access events for a medication package. The lock monitoring service 1706 can update the record in response to receiving a message from the lock device 1702 that indicates that the lock device 1702 has been unlocked. Messages indicating that the lock device 1702 has been unlocked can be forwarded to other entities, such a healthcare provider.

Biometric authentication can be used by the client device 1704 and/or the lock monitoring service 1706 to authenticate a patient prior to executing a lock/unlock command. The client device 1704 can be paired with the lock device 1702 using a short-range communications protocol, such as BLE, NFC, or WI-FI. The client device 1704 can include any network enabled device capable of connecting to the lock device 1702 using a secured short-range communications protocol. For example, a client device 1704 can include a smartphone, tablet, laptop computer, AI (Artificial Intelligence) assistant device, or similar computing devices.

In one example, the lock device 1702 can be configured to include a biometric sensor used to capture a biometric identifier (e.g., a fingerprint) and the biometric identifier can be authenticated using the lock device 1702, or the biometric identifier can be sent to the lock monitoring service 1706 for authentication. The lock device 1702 may communicate with the lock monitoring service 1706 using API requests. For example, representational state transfer (REST) technology or Simple Object Access Protocol (SOAP) technology can be used. REST is an architectural style for distributed hypermedia systems. A RESTful API (which may also be referred to as a RESTful web service) is a web service API implemented using HTTP and REST technology. SOAP is a protocol for exchanging information in the context of Web-based services.

A network used to communicate with the lock monitoring service 1706 can include any useful computing network, including an intranet, the Internet, a local area network, a wide area network, a wireless data network, or any other such network or combination thereof. Components utilized for such a system may depend at least in part upon the type of network and/or environment selected. Communication over the network may be enabled by wired or wireless connections and combinations thereof.

FIG. 18 is a flow diagram illustrating a method for controlling access to a medication package using a locking device. As in block 1802, biometric credentials can be authenticated in response to a request to unlock the locking device. For example, a patient prescribed a pharmaceutical provided in a medication package secured using the locking device, can provide biometric credentials via a client device having a biometric sensor. The client device can be used to authenticate the biometric credentials, or the client device can send the biometric credentials to a lock monitoring service for authentication.

After successful authentication of the biometric credentials, as in block 1804, the client device, or the lock monitoring service, can send an unlock command to a lock device included in the locking device. In response to receiving the unlock command, the lock device can activate a locking mechanism that releases the lock device from a cover, allowing the cover to be removed from a medication package and providing access to the content of the medication package. As in block 1806, an unlock notification can be sent to the lock monitoring service. The notification can be sent by the lock device, or by a client device. The lock monitoring service can update a record and/or forward the notification to other interested parties, such as a healthcare provider. As in block 1808, the lock device can be reengaged by replacing the cover and activating the locking mechanism to a locked position. In one example, the lock device can be configured to reengage the lock after an amount of time has elapsed.

Figure 19:
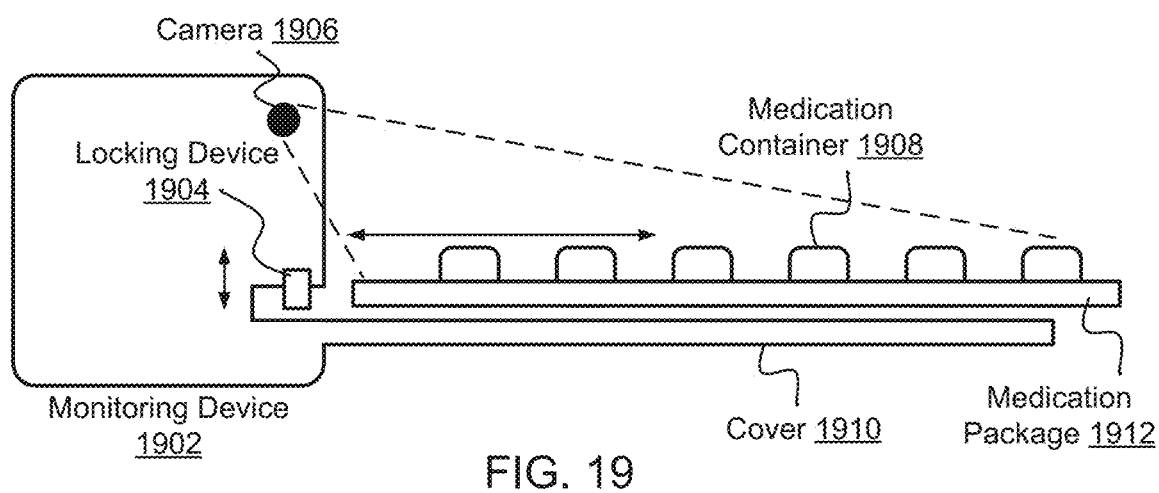
FIG. 19 is a diagram illustrating an example monitoring device that includes a cover and locking device to secure a medication container and monitor the medication container.
Figure 20:
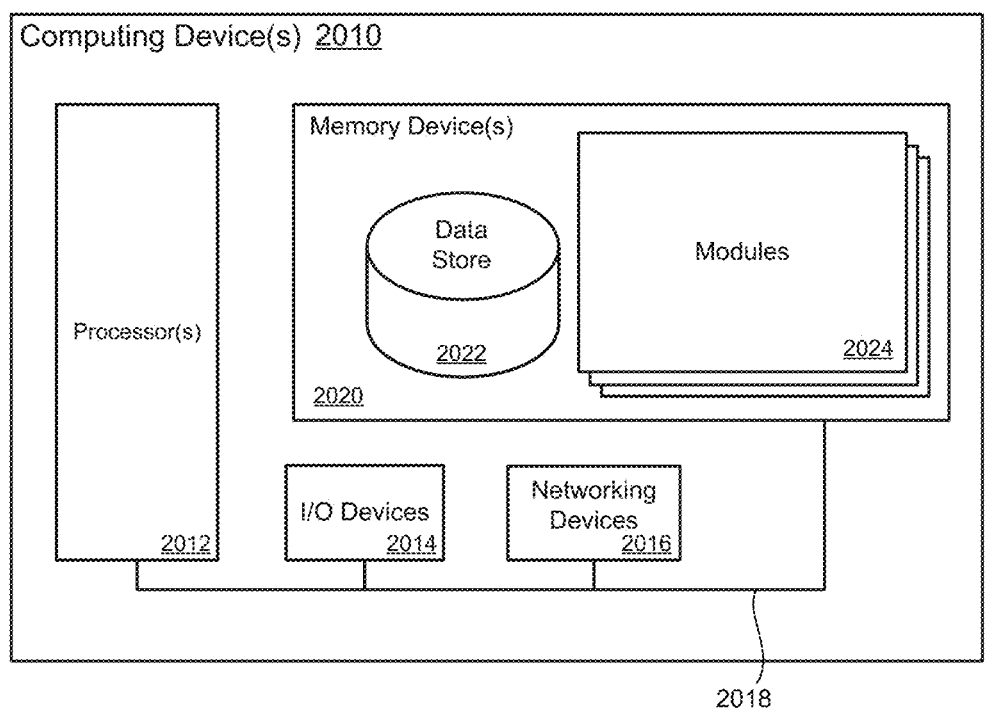
FIG. 20 is block diagram illustrating an example of a computing device that may be used to execute the methods described herein.

FIG. 19 is a diagram illustrating an example monitoring device 1902 configured to secure a medication container 1908 using a cover 1910 and a locking device 1904 and monitor access to the medication container 1908. As illustrated, the monitoring device 1902 described in association with FIGS. 12 and 13 can be configured to include the cover 1910 and locking device 1904 described in association with FIGS. 16 and 17.

In one example, the monitoring device 1902 can be attached to a medication package 1912 so that the cover 1910 engages a portion of the medication package 1912 that provides access to a pharmaceutical contained in a medication container 1908. For example, the cover 1910 can comprise a tray portion configured to hold the medication package 1912, and the cover portion may block access to the face of the medication package 1912 that provides access to medication containers 1908 containing a pharmaceutical. The medication package 1912 can include an attachment point where the lock device 1904 can be engaged and locked to the medication container 1908, thereby preventing access to the medication containers 1908 in the medication package 1912. For example, the medication package 1912 may include a punch-out or hole through which the locking device 1904 can be engaged, or the locking device 1904 can be pressed against the medication package 1912 to lock the medication package 1912 to the monitoring device 1902. The locking device 1904 can be locked and unlocked as described earlier in association with FIGS. 16-18.

After attaching the monitoring device 1902 to the medication package 1912, a camera 1906 included in the monitoring device 1902 can be used to monitor the medication containers 1908 included in the medication package 1912 as described earlier in association with FIGS. 12-15. Also, in one example, the monitoring device 1902 can be configured to capture one or more images of medication containers 1908 in response to locking and unlocking the locking device 1904. The images can be compared to determine whether a medication container 1908 has been accessed. For example, a first image captured in response to a request to unlock the locking device 1904) can be compared with a second image captured after relocking the locking device 1904 to determine whether any of the medication containers 1908 have been accessed (e.g., via deformation of a medication container 1908 or detecting that a medication container 1908 is empty), or whether any medication container seals (e.g., blister seals) have been opened or broken. In the case that a determination is made that one or more medication containers 1908 have been accessed, the monitoring device 1902 can perform the actions described earlier.

EXAMPLES

In one example there is provided a controller to detect a change in a state of a medication container indicating access to the medication container, the controller comprising circuitry to process instructions, that when executed:

analyze images of the medication container to determine a change in the state of the medication container;

detect a change in the state of the medication container indicating that the medication container has been accessed; and initiate sending of a notification indicating that the medication container has been accessed.

In one example of the controller, the images of the medication container are analyzed to detect a change in shape or volume of the medication container.

In one example of the controller, the controller is integrated in a monitoring device that is attachable to the medication container, and the controller is coupled to a camera configured to generate the images of the medication container when the monitoring device is attached to the medication container.

In one example of the controller, the controller is coupled to a locking device configured to block access to the medication container, and the instructions, when executed, further:

receive a request to access the medication container;

authenticate an identifier included in the request to access the medication container; and send an unlock command to the locking device when authentication of the identifier is successful.

In one example there is provided a monitoring device for monitoring a medication container, comprising:

at least one processor;

a camera;

a memory device including instructions that, when executed by the at least one processor, cause the monitoring device to:

activate the camera in response to detecting a change in orientation of the monitoring device;

monitor the medication container using images of the medication container captured by the camera to determine whether the medication container has been accessed;

determine that the medication container has been accessed; and initiate an update to a record to indicate that the medication container has been accessed.

In one example of the monitoring device, the memory device includes instructions that, when executed by the processor, cause the monitoring device to further initialize the record in non-volatile memory included in the monitoring device as part of attaching the monitoring device to the medication container, wherein the record indicates a configuration of the medication container, an access indicator, and an access time.

In one example of the monitoring device, the memory device includes instructions that, when executed by the processor, cause the monitoring device to further monitor an orientation of the monitoring device using a gyroscope included in the monitoring device.

In one example of the monitoring device, determining that the medication container has been accessed further comprises, comparing a first image of the medication container with a second image of the medication container to determine whether a state of the medication container has changed.

In one example of the monitoring device, the medication container is a blister package, and a determination that a blister in the blister package has been accessed includes comparing a first image of the blister with a second image of the blister to determine whether the blister has been deformed.

In one example of the monitoring device, the medication container is a blister package, and a determination that a blister in the blister package has been accessed further comprises, comparing a first image of a blister seal with a second image of the blister seal to determine whether the blister seal has been broken.

In one example of the monitoring device, the memory device includes instructions that, when executed by the processor, cause the monitoring device to further send the record, via a network, to a package monitoring service configured to track access to the medication container to determine whether a medication is being dispensed according to a medication prescription.

In one example of the monitoring device, wherein the monitoring device further comprises:

a cover configured to engage a portion of the medication container blocking access to content of the medication container; and a lock device configured to secure the cover to the medication container.

In one example of the monitoring device, the memory device includes instructions that, when executed by the processor, cause the monitoring device to further:

authenticate an identifier included in an unlock request to access the medication container; and send an unlock command to the locking device when authentication of the identifier is successful.

In one example of the monitoring device, the identifier included in the unlock request is a biometric identifier.

In one example of the monitoring device, the lock device includes a locking mechanism that is controlled via commands received over a network.

In one example of the monitoring device, the identifier included in the unlock request is received from a trusted device.

In one example of the monitoring device, the identifier included in the unlock request is a biometric identifier received from the trusted device.

In one example of the monitoring device, the memory device includes instructions that, when executed by the processor, cause the monitoring device to further provide alternative unlocking instructions when authentication of the identifier is unsuccessful.

In one example of the monitoring device, the memory device includes instructions that, when executed by the processor, cause the monitoring device to further initiate sending of a message to a lock monitoring service indicating access to the medication container.

In one example of the monitoring device, the memory device includes instructions that, when executed by the processor, cause the monitoring device to further:

detect attempted unauthorized access to the medication container; and initiate sending of an alert, via a network, to a lock monitoring service indicating the attempted unauthorized access to the medication container.

In one example there is provided a non-transitory machine readable storage medium including instructions embodied thereon for a monitoring service, the instructions when executed by one or more processors:

receive images of a medication container captured using a camera included in a monitoring device configured to monitor the medication container and send the images to the monitoring service;

analyze the images to determine whether the medication container has been accessed indicating that content contained in the medication container has been removed;

determine that the medication container has been accessed; and update a record to indicate that the content contained in the medication container has been removed.

In one example of the non-transitory machine readable storage medium, the instructions when executed by the one or more processors cause the one or more processors to further:

obtain a medication prescription for the content of the medication container from a patient prescription service; and determine whether the content of the medication container is being used according to the medication prescription.

In one example of the non-transitory machine readable storage medium, the instructions when executed by the one or more processors cause the one or more processors to further:

receive a request to access the medication container having a locking device engaged to a portion of the medication container which provides access to content of the medication container;

authenticate an identifier included in the request to access the medication container; and send an unlock command to the locking device when authentication of the identifier is successful.

In one example of the non-transitory machine readable storage medium, the monitoring service is hosted in a computing service environment.

In one example of the non-transitory machine readable storage medium, the monitoring service is hosted on a mobile device.

In one example there is provided, a blister package locking device, comprising:

a blister pack cover configured to engage a portion of a blister package providing access to blister cavities; and a network connected lock device configured to secure the blister pack cover to the blister package, wherein the network connected lock device includes a locking mechanism that is controlled via commands received over a network.

In one example of the blister package locking device, the network connected lock is configured to detect unauthorized access to the blister package and send an alert to a lock monitoring service indicating attempted access to the blister package.

In one example there is provided, a system for securing a blister package, comprising:

at least one processor;

a memory device including instructions that, when executed by the at least one processor, cause the system to:

receive a request to access a blister pack having a blister pack locking device engaged to a portion of the blister pack which provides access to blister cavities included in the blister pack;

authenticate an identifier included in the request to access the blister pack; and send an unlock command to the blister pack locking device when authentication of the identifier is successful.

In one example of the system for securing a blister package, the identifier included in the request to access the blister pack is a biometric identifier.

In one example of the system for securing a blister package, the identifier included in the request to access the blister pack is received from a trusted device.

In one example of the system for securing a blister package, the identifier included in the request to access the blister pack is a biometric identifier received from a trusted device.

In one example of the system for securing a blister package, the memory device includes instructions that, when executed by the processor, cause the system to further send a message to a lock monitoring service indicating access to the blister package.

In one example of the system for securing a blister package, the memory device includes instructions that, when executed by the processor, cause the system to further provide alternative unlocking instructions when authentication of the identifier is unsuccessful.

FIG. 19 illustrates a computing device 1910 on which modules of the technology described in this disclosure may execute. A computing device 1910 is illustrated on which a high level example of the technology may be executed. The computing device 1910 may include one or more processors 1912 that are in communication with memory devices 1920. The computing device 1910 may include a local communication interface 1918 for the components in the computing device. For example, the local communication interface 1918 may be a local data bus and/or any related address or control busses as may be desired.

The memory device 1920 may contain modules 1924 that are executable by the processor(s) 1912 and data for the modules 1924. For example, the memory device 1920 can include an activation module, a monitoring and instructions module, an analysis and instructions module, and other modules. The modules 1924 may execute the functions described earlier. A data store 1922 may also be located in the memory device 1920 for storing data related to the modules 1924 and other applications along with an operating system that is executable by the processor(s) 1912.

Other applications may also be stored in the memory device 1920 and may be executable by the processor(s) 1912. Components or modules discussed in this description that may be implemented in the form of software using high-level programming languages that are compiled, interpreted or executed using a hybrid of the methods.

The computing device 1910 may also have access to I/O (input/output) devices 1914 that are usable by the computing device 1910. Other known I/O devices may be used with the computing device 1910 as desired. Networking devices 1916 and similar communication devices may be included in the computing device. The networking devices 1916 may be wired or wireless networking devices that connect to the internet, a LAN, WAN, or other computing network.

The components or modules that are shown as being stored in the memory device 1920 may be executed by the processor(s) 1912. The term "executable" may mean a program file that is in a form that may be executed by a processor 1912. For example, a program in a higher level language may be compiled into machine code in a format that may be loaded into a random access portion of the memory device 1920 and executed by the processor 1912, or source code may be loaded by another executable program and interpreted to generate instructions in a random access portion of the memory to be executed by a processor. The executable program may be stored in any portion or component of the memory device 1920. For example, the memory device 1920 may be random access memory (RAM), read only memory (ROM), flash memory, a solid state drive, memory card, a hard drive, optical disk, floppy disk, magnetic tape, or any other memory components.

The processor 1912 may represent multiple processors and the memory 1920 may represent multiple memory units that operate in parallel to the processing circuits. This may provide parallel processing channels for the processes and data in the system. The local interface 1918 may be used as a network to facilitate communication between any of the multiple processors and multiple memories. The local interface 1918 may use additional systems designed for coordinating communication such as load balancing, bulk data transfer and similar systems.

While the flowcharts presented for this technology may imply a specific order of execution, the order of execution may differ from what is illustrated. For example, the order of two more blocks may be rearranged relative to the order shown. Further, two or more blocks shown in succession may be executed in parallel or with partial parallelization. In some configurations, one or more blocks shown in the flow chart may be omitted or skipped. Any number of counters, state variables, warning semaphores, or messages might be added to the logical flow for purposes of enhanced utility, accounting, performance, measurement, troubleshooting or for similar reasons.

Some of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of executable code may, for instance, comprise one or more blocks of computer instructions, which may be organized as an object, procedure, or function. Nevertheless, the executables of an identified module need not be physically located together, but may comprise disparate instructions stored in different locations which comprise the module and achieve the stated purpose for the module when joined logically together.

Indeed, a module of executable code may be a single instruction or many instructions and may even be distributed over several different code segments, among different programs and across several memory devices. Similarly, operational data may be identified and illustrated herein within modules and may be embodied in any suitable form and organized within any suitable type of data structure. The operational data may be collected as a single data set, or may be distributed over different locations including over different storage devices. The modules may be passive or active, including agents operable to perform desired functions.

The technology described herein may also be stored on a computer readable storage medium that includes volatile and non-volatile, removable and non-removable media implemented with any technology for the storage of information such as computer readable instructions, data structures, program modules, or other data. Computer readable storage media include, but is not limited to, non-transitory media such as RAM, ROM, EEPROM, flash memory or other memory technology, optical storage, magnetic storage devices, or any other computer storage medium which may be used to store the desired information and described technology.

The devices described herein may also contain communication connections or networking apparatus and networking connections that allow the devices to communicate with other devices. Communication connections are an example of communication media.

Communication media typically embodies computer readable instructions, data structures, program modules and other data in a modulated data signal such as a carrier wave or other transport mechanism and includes any information delivery media. A "modulated data signal" means a signal that has one or more of its characteristics set or changed in such a manner as to encode information in the signal. By way of example and not limitation, communication media includes wired media such as a wired network or direct-wired connection and wireless media such as acoustic, radio frequency, infrared and other wireless media. The term computer readable media as used herein includes communication media.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

What is claimed is:

1. An authenticator device to authorize release of an active agent using an ingestible pill device, the authenticator device comprising:
   at least one memory; and
   at least one processor to execute instructions to:
      obtain an identifier transmitted from the ingestible pill device, wherein the identifier is stored on the ingestible pill device;
      authenticate the identifier transmitted by the ingestible pill device;
      obtain a first sensor signal from a first sensor coupled to the ingestible pill device;
      analyze the first sensor signal to determine whether one or more first conditions to release the active agent are fulfilled;
      obtain a second sensor signal from a second sensor coupled to the ingestible pill device, the second sensor signal associated with gastrointestinal (GI) image data;
      analyze the GI image data from the second sensor signal to identify a physical attribute corresponding to one or more second conditions to the release of the active agent, the physical attribute including an active agent release point located in a GI tract that is indicative of when an instruction to release the active agent is to be sent to the ingestible pill device; and
      send the instruction to the ingestible pill device to release the active agent contained in the ingestible pill device when authentication of the identifier is successful and when the one or more first conditions and the one or more second conditions are fulfilled.

2. The authenticator device in claim 1, wherein the at least one processor is to obtain a patient identifier stored in the memory, wherein the patient identifier is to authenticate the identifier transmitted by the ingestible pill device by determining whether the identifier transmitted by the ingestible pill device corresponds to the patient identifier.

3. The authenticator device in claim 1, wherein the at least one processor is to:
   obtain patient credentials; and
   authenticate the patient credentials, wherein the at least one processor is to authenticate the identifier and of the patient credentials to allow the instruction to release the active agent to be sent to the ingestible pill device.

4. The authenticator device in claim 3, further including a user interface to obtain the patient credentials.

5. The authenticator device in claim 3, wherein the at least one processor is to authenticate the patient credentials using patient information stored in the memory.

6. The authenticator device in claim 3, wherein the at least one processor is to send the patient credentials to a drug provisioning service to authenticate the patient credentials.

7. The authenticator device in claim 1, wherein the at least one processor is to:
   cause establishment of a link with the ingestible pill device using a pairing mechanism;
   provide a prompt for at least one of an authentication question, a password, or a PIN (Personal Identification Number); and
   authenticate the at least one of the authentication question, the password, or the PIN.

8. The authenticator device in claim 1, wherein the at least one processor is to establish a network connection with the ingestible pill device using a pairing process that uses the identifier transmitted by the ingestible pill device as a pairing code, wherein successful pairing using the identifier as the pairing code authenticates the identifier transmitted by the ingestible pill device.

9. The authenticator device in claim 1, wherein the at least one processor is to:
obtain an encryption key stored in the memory; and
decrypt the identifier transmitted by the ingestible pill device using the encryption key.

10. The authenticator device in claim 1, wherein the first sensor signal from the ingestible pill device is associated with pH data, the at least one processor to analyze the pH data to determine whether the pH data meets a pH threshold condition that allows the instruction to release the active agent to be sent to the ingestible pill device.

11. The authenticator device in claim 1, wherein the first sensor signal from the ingestible pill device is associated with chemical sensor data, the at least one processor to identify a chemical attribute condition based on the chemical sensor data, satisfaction of the chemical attribute condition to allow the instruction to release the active agent to be sent to the ingestible pill device.

12. The authenticator device in claim 1, wherein the at least one processor is to:
obtain dosing instructions from a patient prescription service via a network; and
cause transmission of the dosing instructions to the ingestible pill device to enable the ingestible pill device to release the active agent according to the dosing instructions.

13. The authenticator device in claim 12, wherein the at least one processor is to cause the instruction to release the active agent contained in the ingestible pill device to be sent at staged intervals according to the dosing instructions, wherein the ingestible pill device is to release a defined amount of the active agent during each staged interval.

14. The authenticator device in claim 12, wherein the dosing instructions specify an amount of the active agent to release.

15. The authenticator device in claim 1, wherein the instruction to the ingestible pill device to release the active agent is to activate the ingestible pill device prior to ingestion of the ingestible pill device and the ingestible pill device is to release the active agent after the one or more first conditions and the one or more second conditions are fulfilled.

16. The authenticator device in claim 15, wherein the ingestible pill device is activated prior to ingestion using a Near Field Communication (NFC) enabled device.

17. The authenticator device in claim 1, wherein the at least one processor does not cause transmission of the instruction to release the active agent contained in the ingestible pill device to the ingestible pill device when authentication of the identifier fails or when one or more the first conditions or the second conditions are not fulfilled.

18. The authenticator device in claim 1, wherein the at least one processor is to:
obtain an indication from the ingestible pill device that the active agent was released; and
cause a record to be generated indicating that the active agent was released.

19. The authenticator device in claim 1, further including a short-range communication device to use a short-range communications protocol to communicate with the ingestible pill device.

20. The authenticator device in claim 1, further including a networking device to connect to a data network used to communicate with the ingestible pill device.

21. The authenticator device in claim 1, wherein the authenticator device is a subdermal implantable device that includes a transceiver to communicate with the ingestible pill device.

22. The authenticator device in claim 1, wherein the authenticator device is a mobile device that is communicatively couplable with the ingestible pill device.

* * * * *